United States Patent
Shishido et al.

(10) Patent No.: US 7,456,963 B2
(45) Date of Patent: *Nov. 25, 2008

(54) METHOD AND EQUIPMENT FOR DETECTING PATTERN DEFECT

(75) Inventors: Hiroaki Shishido, Yokohama (JP); Yasuhiro Yoshitake, Yokosuka (JP); Toshihiko Nakata, Hiratsuka (JP); Shunji Maeda, Yokohama (JP); Minoru Yoshida, Yokohama (JP); Sachio Uto, Yokohama (JP)

(73) Assignee: Hitachi, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/593,091

(22) Filed: Nov. 6, 2006

(65) Prior Publication Data

US 2007/0052955 A1    Mar. 8, 2007

Related U.S. Application Data

(63) Continuation of application No. 11/184,981, filed on Jul. 20, 2005, now Pat. No. 7,132,669, which is a continuation of application No. 10/947,262, filed on Sep. 23, 2004, now Pat. No. 6,921,905, which is a continuation of application No. 09/473,296, filed on Dec. 28, 1999, now Pat. No. 6,800,859.

(30) Foreign Application Priority Data

Dec. 28, 1998 (JP) .................................. 10-372769
Sep. 17, 1999 (JP) .................................. 11-262997

(51) Int. Cl.
G01J 4/00 (2006.01)
(52) U.S. Cl. .................................. 356/369; 356/364

(58) Field of Classification Search .................... None
See application file for complete search history.

(56) References Cited

U.S. PATENT DOCUMENTS

| 5,264,700 | A |   | 11/1993 | Tommasini et al. |
|-----------|---|---|---------|------------------|
| 5,264,912 | A |   | 11/1993 | Vaught et al. |
| 5,331,169 | A |   | 7/1994  | Tanaka et al. |
| 5,486,919 | A | * | 1/1996  | Tsuji et al. ............... 356/237.4 |
| 5,625,193 | A |   | 4/1997  | Broude et al. |
| 5,774,222 | A |   | 6/1998  | Maeda et al. |
| 6,040,909 | A | * | 3/2000  | Hasegawa et al. ........... 356/614 |
| 6,256,087 | B1|   | 7/2001  | Bader |

(Continued)

FOREIGN PATENT DOCUMENTS

JP        56-62219        5/1981

(Continued)

Primary Examiner—Gregory J Toatley, Jr.
Assistant Examiner—Juan D Valentin
(74) Attorney, Agent, or Firm—Antonelli, Terry, Stout & Kraus, LLP.

(57) ABSTRACT

An Inspection apparatus and method includes utilizing an emitter which emits a light beam, an illumination optical system, a detection optical system, and a processor. The illumination optical system includes a polarization controller, a coherence reducer, and an objective lens, for illuminating a specimen with a polarization condition controlled and coherency reduced light beam through the objective lens. The detection optical system includes an imaging lens and a sensor for detecting an image of the specimen illuminated by the light beam through the illumination optical system. The processor processes a signal outputted from the sensor and detects a defect on the specimen.

6 Claims, 23 Drawing Sheets

U.S. PATENT DOCUMENTS 6,369,888 B1  4/2002  Karpol et al.

FOREIGN PATENT DOCUMENTS

| JP | 62-90615 | 4/1987 |
| JP | 62-109019 | 5/1987 |
| JP | 5-289014 | 11/1993 |
| JP | 6-102462 | 4/1994 |
| JP | 11-218991 | 8/1999 |

* cited by examiner

AS

FS

AS

FS

AS

FA

AS

FS

AS

FS

AS

Ts < Ti

FS

AS

Ts < Ti × N

FS $\Delta \lambda_1$ $\Delta \lambda_2$

US 7,456,963 B2

METHOD AND EQUIPMENT FOR DETECTING PATTERN DEFECT

CROSS REFERENCE TO RELATED APPLICATION

This is a continuation of U.S. application Ser. No. 11/184,981, filed Jul. 20, 2005, now U.S. Pat. No. 7,132,669, which is a continuation of U.S. application Ser. No. 10/947,262, filed Sep. 23, 2004, now U.S. Pat. No. 6,921,905, which is a continuation of U.S. application Ser. No. 09/473,296, filed Dec. 28, 1999, now U.S. Pat. No. 6,800,859, the subject matter of which is incorporated by reference herein.

BACKGROUND OF THE INVENTION

The present invention relates to a method and equipment for detecting a pattern defect; and, more specifically, the invention relates to a method and equipment suitable to detect and test a defect of a pattern formed in a semiconductor wafer, a liquid crystal display, a photomask, etc.

Conventionally, detecting equipment, such as described in Japanese Published Unexamined Patent Application No. 7-318326 (prior art No. 1), scans an image of a pattern under test (hereinafter referred to as a "test pattern" for simplicity) using an imager, such as a line sensor etc., and is able to recognized nonconformity as a defect by comparing grayscale levels of the detected image signal to an image signal delayed by a prescribed time while moving the test pattern.

Moreover, a conventional technology concerning detection of a defect in a test pattern is disclosed in Japanese Published Unexamined Patent Application No. 8-320294 (prior art No. 2). This prior art 2 is intended to be applied to a test pattern on a semiconductor wafer etc. where a high density area of the test pattern, such as a memory mat part etc., and a low density area of the test pattern, such as a peripheral circuit etc., exist in a mixed manner. This publication describes a method comprising the steps of: converting a digital image signal that is obtained through AD conversion of an image signal detected from the above-described test pattern into grayscale levels so that the brightness or the contrast ranging between the high density area and the low density area of the test pattern is converted into a predetermined relation based on a brightness-frequency relationship of the above-described detected image signal; performing a function approximation on both the image signal thus grayscale converted and an image signal to be compared (hereinafter referred to as a "comparison image signal") therewith, which was also grayscale converted; integrating the difference between the two curves represented by the function approximations; aligning two image signals which were grayscale converted based on information of high-precision detection of misalignment obtained from the integral value; and detecting a minute defect with high-precision by comparing test patterns while keeping the alignment between two image signals optimally.

Moreover, in the case of detecting a photomask, conventionally it has been proposed that the light used in the detecting should be the same as the exposure light so as to detect only a detrimental defect which will cause trouble in the actual exposure; accordingly, with this in mind, it has been suggested that inspection of a photomask exposed with ultraviolet light (hereinafter referred to as "UV light") should be performed using the same UV light as the exposure light. Patent applications concerning this technology, as a technology to test the appearance of a circuit pattern on a photomask, include Japanese Published Unexamined Patent Application No. 8-94338 (prior art No. 3) and No. 10-78668 (prior art No. 4).

In addition, a technology to measure the amount of phase shift in a phase shift mask is disclosed in Japanese Published Unexamined Patent Application No. 10-62258 (prior art No. 5) and No. 10-78648 (prior art No. 6).

Furthermore, a technology to clearly visualize a circuit pattern and a foreign material optically by inspecting a specimen with visible light and UV light by making good use of a fact that materials used in a process have different absorption characteristics for visible light and UV light is disclosed in Japanese Published Unexamined Patent Application No. 4-165641 (prior art No. 7) and No. 4-282441 (prior art No. 8).

Moreover, means for measuring optically an external form of an object using an interferometer is disclosed in Japanese Published Unexamined Patent Application No. 4-357407 (prior art No. 9), wherein UV light is applied to the interferometer.

LSI fabrication in recent years has progressed toward finer microfabrication in circuit patterns formed on wafers in response to a need for high-integration, and a pattern having a width (feature size) as small as 0.25 µm or less is being required, reaching almost a limit of the available imaging optical systems. Therefore, efforts to attain a high NA in an imaging optical system and to apply the optical super-resolution technology, as well as efforts to provide more sophisticated image processing, are being made. The above-described prior arts 1 and 2 are directed to techniques that use those results. However, implementation of a high NA has already reached its physical limit, and this measure has a problem of weakness for patterns having a large pattern step height. Also, the optical super-resolution technology and sophistication of image processing have a problem of limited applicability because of their non-linear response.

Therefore, an attempt to shorten the wavelength of light used in defect detection, from a visible radiation region in conventional use to a UV light region, is an essential approach.

On the other hand, the idea that the same light source as exposure light should be used, which has been originally devised for a photomask, is effective for prior arts 5 and 6 for measuring the amount of phase shift. This is because the amount of phase shift is directly linked with the wavelength of the light source. However, in case defects are to be detected by detecting the appearance of the whole surface of a test sample or a large area of a circuit pattern comparable to it, the technology wherein a wavelength of detecting light is chosen to be the same as the exposure light (prior arts 3 and 4) is not necessarily an appropriate technique.

This is because the pattern transfer capability by exposure cannot be determined only by the wavelength of the light source and the conditions of the optical system. The transfer capability is closely connected with various factors in a complicated way, such as the amount of exposure, properties of a resist, the amount of defocusing, an optical characteristic of an underlying material, a developing process, etc. Consequently, the prior arts 3 and 4 are directed to techniques which are suitable to analyze carefully the pattern transfer capability of a single defect by performing a simulation including these complicated conditions, but are different from a technology for detecting defects of a large number of circuit patterns in a short period of time.

In the case where a large number of circuit patterns are examined in a short time, it will be a practical solution for this problem to thoroughly detect any defects having a possibility of being transferred as a detectable defect with a sensitivity as high as possible by means of a light source that is chosen only to detect defects, rather than performing a detection by applying an expensive, hard-to-handle exposure light source.

In this case, since UV light is employed to improve the resolution, visible light that deteriorates the resolution cannot be employed jointly as is the case of the prior arts 7 and 8.

Further, since it is essential to perform a rapid detecting, a minutely converged laser beam as in the prior art 9 cannot be used. In the UV light region, since a high-illuminance discharge lamp does not exist, a high-illuminance illumination by means of a laser is indispensable. However, as a result, when a laser beam is expanded to a whole field of view, an interference fringe pattern due to interference of the laser beam, a so-called speckle pattern, occurs and overshoot and undershoot occur in edge-portions of a circuit pattern, which make it impossible to obtain images.

Laser beams have excellent features as light sources. To use them in a way which will give their features full play, when a certain area is illuminated, generally the laser beams are scanned using some kind of scanning means.

For the scanning means, there are means capable of scanning by driving a mirror mechanically to change a reflection direction, means capable of scanning by applying an electric signal to an optical crystal to effect a change in diffraction direction or in refraction direction, and the like.

Among the former means, there exist a galvano mirror, a polygon mirror (a polyhedron mirror), etc., and among the latter means, there exist an A/O deflector, an E/O deflector, etc.

Japanese Published Unexamined Patent Application No. 7-201703 discloses equipment to scan a laser beam using a polygon mirror or a galvano mirror and to write a pattern with a minutely converged laser spot. Further, Japanese Published Unexamined Patent Application No. 8-15630 discloses equipment to scan a laser beam using a polygon mirror or an A/O deflector write to a pattern with a minutely converged laser spot. Furthermore, Japanese Published Unexamined Patent Application No. 10-142538 discloses equipment to write a pattern with a minutely converged laser spot in a scheme where two polygon mirrors are set in synchronization with each other, a phase difference of half the period between mirror facets being set, to perform the scanning, and further these polygon mirrors are switched between one another, so that a combination of polygon mirrors scans a laser beam with improved efficiency. Furthermore, Japanese Published Unexamined Patent Application No. 7-197011 discloses a device wherein two polygon mirrors are stacked up with a phase difference of half the period between mirror facets thereof being set and a semiconductor laser diode is modulated in synchronization with its rotation. Furthermore, Japanese Published Unexamined Patent Application No. 5-34621 discloses a device wherein mirror facet angles of a polygon mirror are varied from facet to facet, so that two-dimensional beam scanning can be performed.

The scanning by a polygon mirror (polyhedron mirror) has a problem in that since the scanning is performed under continuous rotation, the scanning is unavailable at the edges of mirror facets, the effective scanning time is decreased, and as a result a decrease inefficiency is brought about.

Moreover, if high-speed scanning is intended, a plurality of polygon mirrors cannot be rotated in synchronization with each other because of the continuous rotation. Therefore, it is impossible in a high-speed region for a two-dimensional is area to be scanned by integrating polygon mirrors, and for the scanning efficiency of polygon mirrors to be improved in a scheme where two polygon mirrors are used to perform the scanning in synchronization with each other, also with a phase difference of half the period between mirror facets thereof being set, and which are switched over for use, as disclosed in Japanese Published Unexamined Patent Application No. 10-142538.

Further, a method for directly modulating a laser, even in a scheme where two polygon mirrors are stacked up with a phase difference of half the period between mirror facets thereof being set, as disclosed in Japanese Published Unexamined Patent Application No. 7-197011, is not suitable for application in a deep ultraviolet wavelength region, because gas lasers and solid state lasers are not suitable for direct modulation. Further, one such laser is too expensive to make a configuration where a plurality of lasers are arranged and on-off switched instead of being directly modulated.

Further, since a polygon mirror rotates continuously, the scanning range cannot be changed. Therefore, the shape of the range scanned by a polygon mirror is limited to a rectangular area and hence polygon mirrors are not suitable to scan circular regions.

Further, in the wavelength region of deep ultraviolet light sources, there is a problem that a surface irregularity of a polygon mirror causes scattered light, which deteriorates the beam quality and refection efficiency.

As for the scanning by galvano mirrors, ordinary galvano mirrors can only perform low-speed scanning with a scanning speed of a few hundred Hz at maximum, whereas a resonant-type galvano mirror can perform high-speed scanning at a few kHz, but the driving signal is limited only to sinusoidal waves and the scanning angle varies sinusoidally, and therefore the scanning speed of the beam is not constant. Because of this fact, when laser beam scanning is performed for illumination to obtain a detected signal especially using a storage-type sensor, there is a problem in that a signal from a slowly scanned area is relatively large, whereas a signal from a fast scanned area is relatively small.

For E/O deflectors, there is no crystal usable in a wavelength range of ultraviolet to deep ultraviolet light. Therefore, current technology cannot respond to a request for a high-resolution optical system with a light source whose wavelength is shortened.

Moreover, for A/O deflectors there is only quartz for a crystal usable in the range of ultraviolet to deep ultraviolet wavelengths. However, the acoustic velocity in quartz is large. This fact is not a large obstacle when an A/O element is used as a modulator, but becomes a problem when it is used as a deflector. When a diffraction grating is formed in quartz using an acoustic element, a variation of the spacing between the gratings in response to a change of signal frequency applied to the acoustic element is small because of its large acoustic speed.

This means that an angular region in which a deflector can deflect light is small. Since the acoustic velocity in quartz is about 6000 m/s and an upper limit of the signal frequency that can be applied to an acoustic element is around 150 MHz, deflection of only 0.23 degree is achievable provided that the variation range of frequency is ±100 MHz. Therefore, if a sufficient scanning range is intended to be achieved, an extremely long optical path (1 m or more) should be provided. With provision of a long optical path, there arises a problem of deterioration in beam position and beam quality due to an environmental change, such as fluctuation of air in the optical path.

SUMMARY OF THE INVENTION

It is an object of the present invention to provide a method and equipment for detecting a minute circuit pattern rapidly with high resolution in order to solve the above-mentioned problems.

In addition, it is another object of the present invention to provide defect detecting equipment which is capable of detecting defects such as submicroscopic foreign particles, a pattern defect, etc. by scanning a short-wavelength (ranging from ultraviolet to deep ultraviolet) laser beam for illumination over a test object such as a semiconductor wafer etc. at a high speed with high-efficiency and detecting an optical image of the test object.

To achieve the above-mentioned objects, the present invention adopts the following steps of: employing a UV laser source as a light source; setting up means for suppressing the occurrence of a speckle pattern of the UV laser beam in an -optical path; and detecting an image of an object by illuminating the surface of the object with the UV light whose coherence was reduced.

More specifically, as a means for suppressing the occurrence of a speckle pattern of the UV laser beam, one of the following means is intended to be provided: (1) means for converging rays of light from a light source onto a single point on a pupil of an objective lens and scanning the light thus focused on the pupil in exact timing with a storage time of a detector; (2) means for directing UV light emitted from the laser source into a bundle of fibers, each fiber of which is intentionally misaligned to the UV light, and converging rays of light going out of the bundle of fibers onto the pupil of the objective lens; (3) means for directing the light into a group of fibers, each of which has a different length varied by the amount of the coherence length of the laser source or more to other fibers, and converging rays of light going out of the group of the fibers onto the pupil of the objective lens; and (4) means for illuminating the pupil with a combination of the above means.

In other words, the present invention provides pattern defect detecting equipment characterized by comprising: laser source means for emitting an ultraviolet laser beam; coherence reducing means for reducing the coherence of the ultraviolet laser beam emitted from this laser source means; irradiating means for irradiating a sample with the ultraviolet laser beam whose coherence was reduced by the coherence reducing means; image detecting means for detecting an image of the sample irradiated with the ultraviolet laser beam produced by the irradiating means; and defect detecting means for detecting a defect of a pattern formed on the sample based on information concerning the image of the sample detected with this image detecting means.

Further, the present invention provides a method of detecting a pattern defect characterized by comprising the steps of: emitting a laser beam whose wavelength is not longer than 400 rim from a laser source; irradiating a sample with the emitted laser beam through coherence reducing means; detecting an image of the sample irradiated with this laser beam; and detecting a defect of a pattern formed on the sample based on information concerning this detected image of the sample.

Further, to achieve the above-mentioned object, the present invention adopts a configuration wherein a set of polygon mirrors, which are made up by stacking a plurality of polygon mirrors with the phase of mirror facets thereof mutually shifted, is rotated, a laser beam is modulated through an A/O modulator in synchronization with rotation of the above-mentioned polygon mirrors and is switched to either of the polygon mirrors appropriately to perform the scanning for irradiation, so that the object can be scanned at a high speed with a high efficiency even when employing a short-wavelength laser beam that is needed to realize a high-resolution.

DESCRIPTION OF THE PREFERRED EMBODIMENTS

Figure 1:
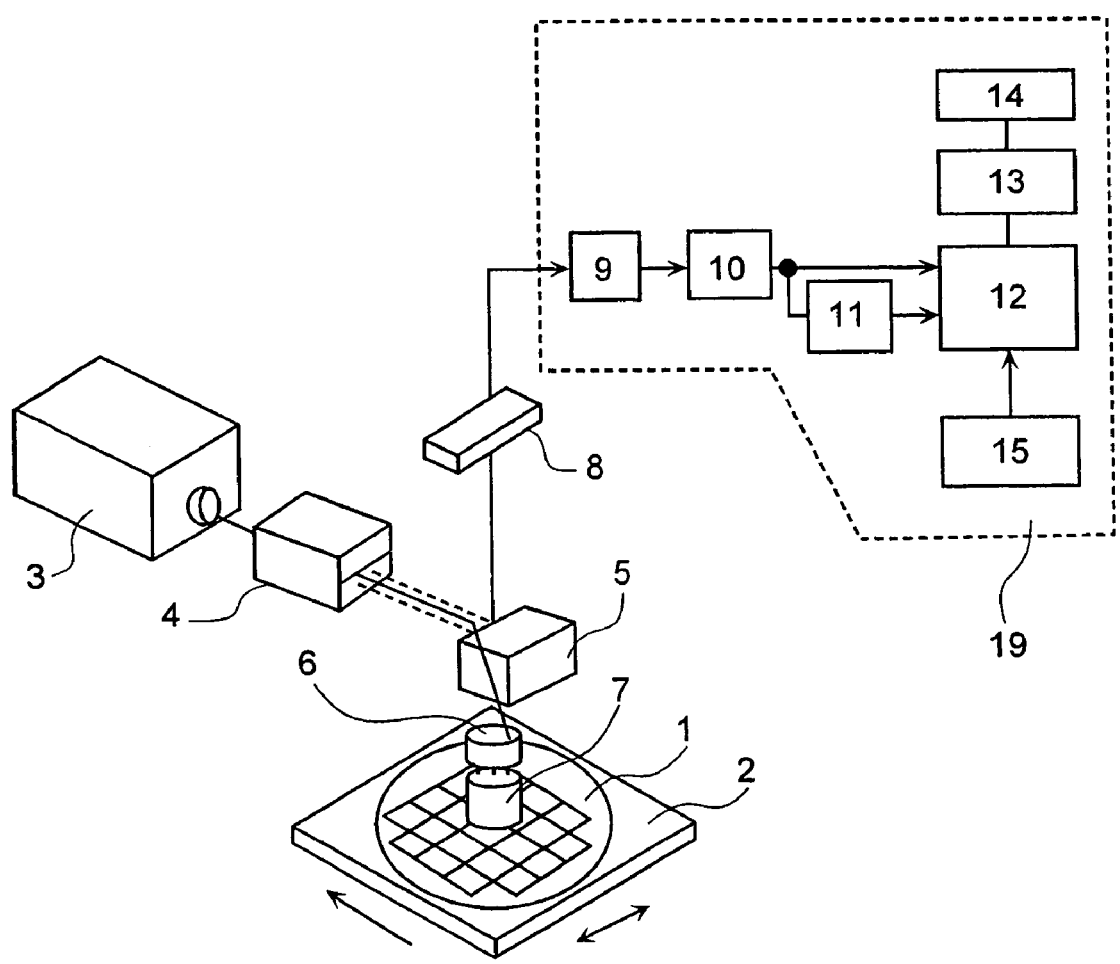
FIG. 1 is a block diagram showing a first embodiment of pattern defect detecting equipment for a test pattern according to the present invention.

Referring to the drawings, a first embodiment of a method and equipment for detecting a pattern defect in a test pattern according to the present invention will be described. FIG. 1 is a block diagram showing a first embodiment of pattern defect detecting equipment according to the present invention. Numeral denotes an X, Y, Z, and θ (rotation) stage, on which a semiconductor wafer 1, an example of a test pattern, is mounted. Numeral 7 denotes an objective lens. Numeral 3 denotes an illumination light source (UV laser source) for illuminating the semiconductor wafer 1, which is an example of a test pattern. Numeral 5 denotes a polarizing beam splitter, which is constructed so as to reflect the illumination light from the illuminating light source 3, make it pass through the objective lens 7, and perform bright field illumination on the semiconductor wafer 1. Numeral 6 denotes a quarter wavelength plate, which forms a high-efficiency half mirror in conjunction with the polarizing beam splitter 5. Numeral 4 denotes a scanning mechanism for scanning a laser beam from the light source over the pupil of the objective lens 7. Numeral 8 denotes an image sensor for outputting a grayscale image signal according to the brightness (grayscale) of reflected light from the semiconductor wafer 1, which is an example of a test pattern. Numeral 9 denotes an AD converter for converting the grayscale image signal obtained from the image sensor 8 into a digital image signal.

While the stage 2 is being moved in a scanning mode and the semiconductor wafer 1, which is an example of the test pattern, is being moved at a constant speed, information of the illuminance (grayscale image signal) of the test pattern formed on the semiconductor wafer 1 is detected with the image sensor 8.

Numeral 10 denotes a grayscale converter for performing such grayscale conversion as is described in Unexamined Japanese Patent Application No. 8-320294 on the digital image signal outputted from the AD converter 9. In other words, the grayscale converter 10 compensates an image, where unevenness of the illuminance has occurred due to thin film interference of the illumination light caused by a thin film formed on the semiconductor wafer by the process by performing logarithmic conversion, index transform, polynomial transform, etc. The grayscale converter 10 is configured so as to output a digital signal in, for example, 8 bits. Numeral 11 denotes a delay memory for storing and delaying an output image signal from the -grayscale converter 10 by the amount of 1 cell or a plural cell pitch, or 1 chip, or 1 shot, wherein a pattern on a semiconductor wafer comprises a plurality of these pattern units.

Numeral 12 denotes a comparator for detecting a defect by comparing the image signal outputted from the grayscale converter 10, on which the grayscale conversion was performed, to a delayed image signal obtained from the delay memory 11.

The comparator 12 is used to compare an image outputted from the delay memory 11 that was delayed by an amount corresponding to a cell pitch etc. to a detected image. By inputting coordinates of the arrangement data etc. on the semiconductor wafer 1 beforehand, which are obtained based on design information, using an inputting means 15 consisting of a key board, a disk drive, etc., CPU 13 produces defect test data from results of comparison by the comparator based on inputted coordinates of array data etc. on the semiconductor wafer 1 and stores them in a storage device 14. This defect test data can be displayed on display means such as display etc. according to need and also can be outputted.

By the way, the comparator may be as is described in Japanese Published Unexamined Patent Application No. 61-212708, for example, the comparator may comprises an image alignment circuit, a difference image detecting circuit for aligned images, a nonconformity detecting circuit for performing a binary coded processing on the difference image, a feature extracting circuit for calculating areas, lengths (projected length), coordinates, etc. from binarized outputs, and the like.

Next, the light source 3 will be described. As described above, in order to attain high resolution, it is necessary to employ a light source having a shorter wavelength. However, in wavelength regions of UV light (ultraviolet light) and DUV light (deep ultraviolet light), where that effect can be maximized, it is rather difficult to have such illumination with high illuminance. Regarding UV light sources, a discharge lamp is excellent. Especially, a mercury xenon lamp has a stronger emission line in the UV region than other discharge lamps.

Figure 2:
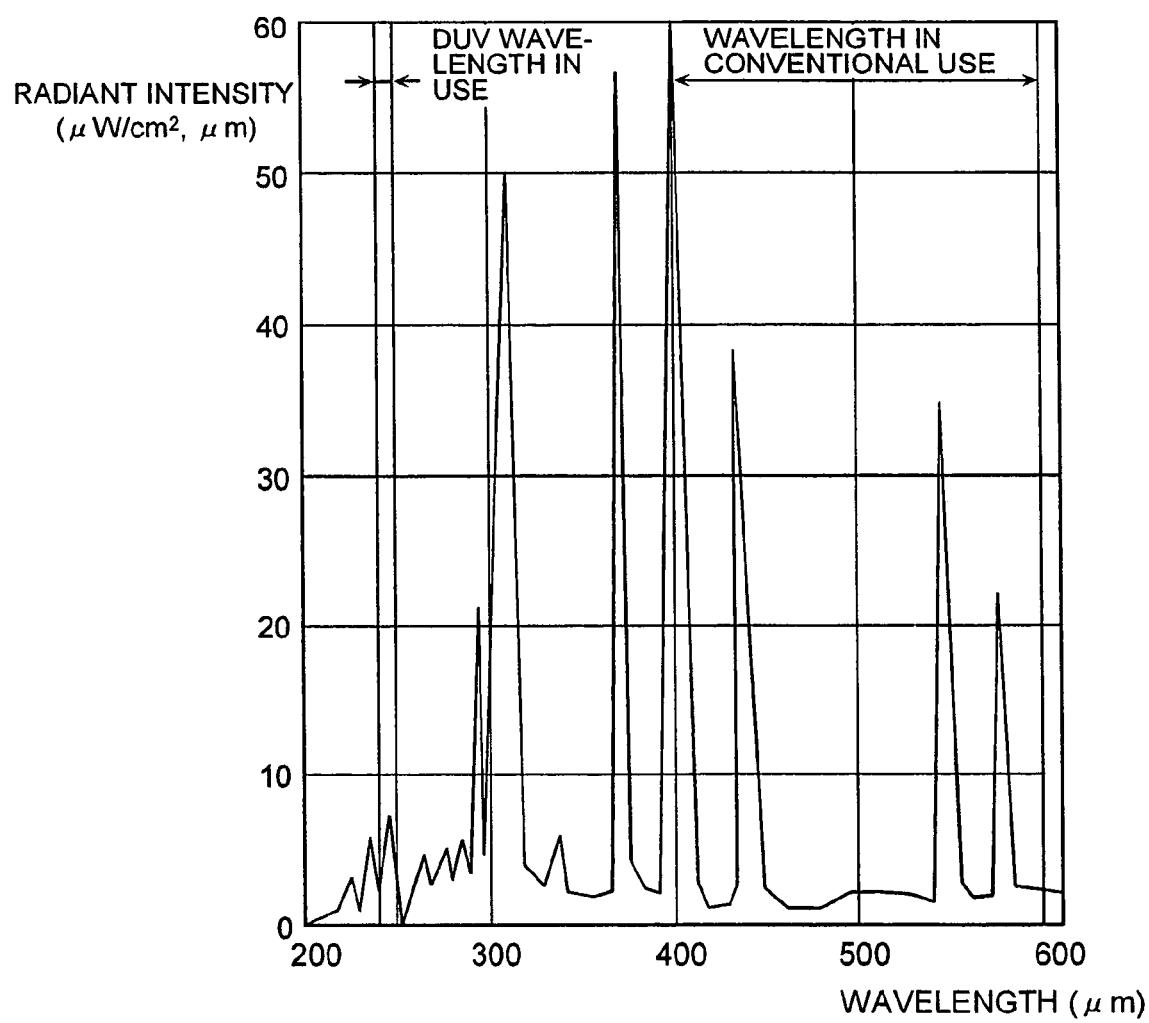
FIG. 2 is a diagram illustrating an emission spectrum of a discharge tube illumination.

FIG. 2 is a diagram showing an example of a relationship of radiant intensity versus wavelength for a mercury xenon lamp, indicating that emission lines in the DUV region occupy only 1-2% of the total amount of radiation, which is in direct contrast to the wide wavelength region of visible light in conventional use (i.e. occupying about 30% of total amount of radiation). In addition, light emitted from a discharge lamp, whose radiation is not oriented in a particular direction, can be guided onto a sample with a significantly small efficiency even in the case of a carefully-designed optical system. After all, a sufficient amount of light can hardly be secured with illumination of a discharge lamp in the UV region.

Moreover, when a discharge lamp having a large output is employed with the intention to improve the intensity of illumination (the illuminance), since such a lamp slightly has a only larger size of a luminescent spot of radiation compared to those having a small output, the illuminance (light power per unit area) cannot be improved with such a scheme.

Consequently, it can be rightly thought that an effective, high-illuminance illumination is optimally performed by a laser source whose center wavelength is in the UV region or in the DUV region (hereinafter UV is used to indicate these two regions) which is not longer than 400 nm, preferably not longer than 300 nm. The present invention provides means for solving such a problem when this UV laser is employed as a light source to illuminate the sample.

Figure 3A:
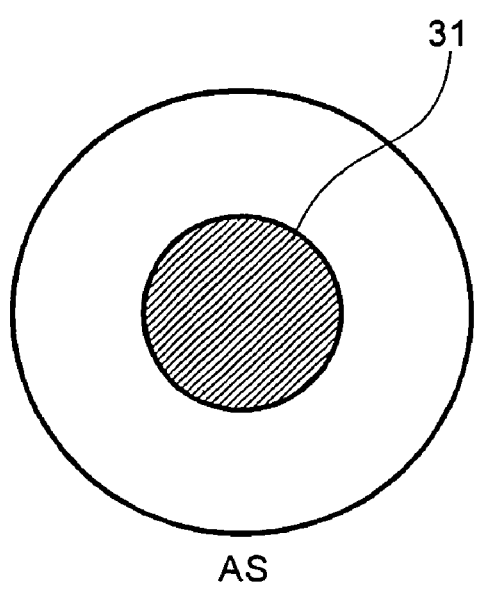
FIG. 3(a) is a diagram showing the illumination condition on the pupil of the detecting objective lens and FIG. 3(b) is a diagram showing the illumination condition in the field of view, both produced by the discharge tube illumination.
Figure 3B:
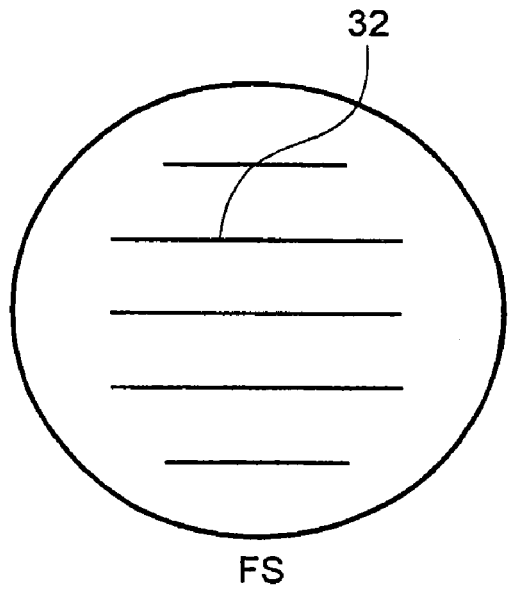

FIG. 3(a) is a diagram showing the illumination condition of the pupil of the objective lens and FIG. 3(b) shows that in the field of view of the sample when illuminated by normal white light. Here, AS denotes the pupil, while FS the field of view. At a position of the pupil, an image 31 of the light source is formed; while, at a position of the field of view, an almost uniformly illuminated area 32 comparable to the whole field of view is formed.

Figure 4A:
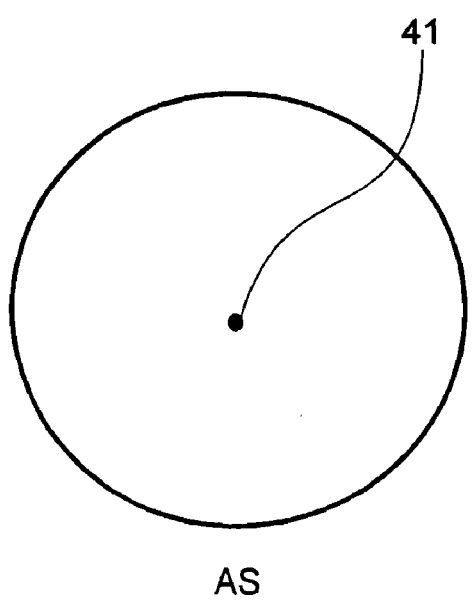
FIG. 4(a) is a diagram showing the illumination condition on the pupil of the detecting objective lens and FIG. 4(b) is a diagram showing the illumination condition in the field of view, both produced by laser beam illumination.
Figure 4B:
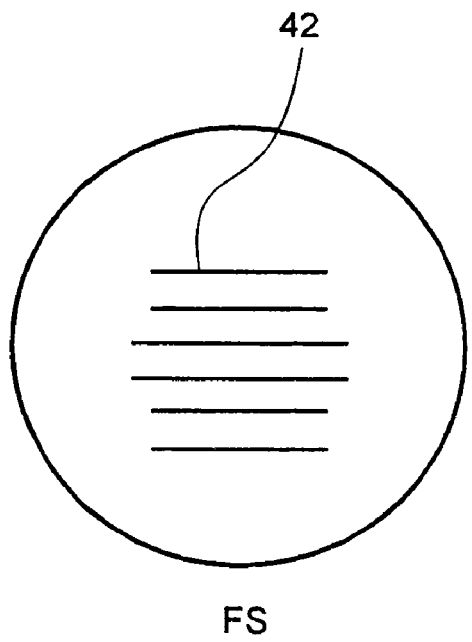
Figure 4C:
FIG. 4(c) is a diagram showing a pattern in the field of view.
Figure 4D:
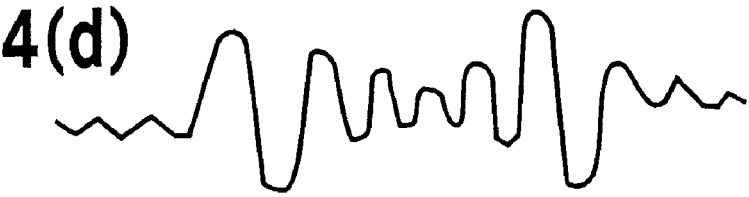
FIG. 4(d) shows a detected signal produced from the pattern of FIG. 4(c).

Next, FIG. 4(a) is a diagram showing the illumination condition of the pupil of the objective lens and FIG. 4(b) shows that of the field of view of the sample when illuminated by a laser source. In this case, the image of the light source 41 at the position of the pupil is reduced to a point. A circuit pattern illuminated by illumination 42 in the field of view on the sample creates, for example, an image having such a detection waveform, as seen in FIG. 4(d) for a pattern whose cross section is as shown in FIG. 4(c).

As can be seen from the drawing, an overshoot and undershoot occur in edge portions of a circuit pattern and a speckle pattern occurs when a circuit pattern is illuminated by a laser beam and its image is taken in such that σ of the illumination is small. In other words, this can result from the fact that illumination is not performed from various angles in the field of view on the sample under the objective lens. On the contrary, in a normal white light illumination, illumination having a certain size of its image on the pupil is produced, and illumination is produced in the field of view on the sample from all directions at an angle comparable to the NA (the numerical aperture) of the objective lens.

Figure 5A:
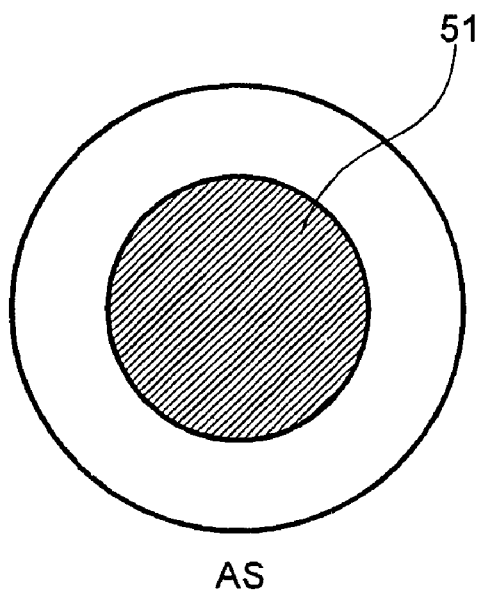
FIG. 5(a) is a diagram showing the illumination condition on the pupil of the detecting objective lens and FIG. 5(b) is a diagram showing the illumination condition in the field of view, both produced by laser beam illumination expanded on the pupil.
Figure 5B:
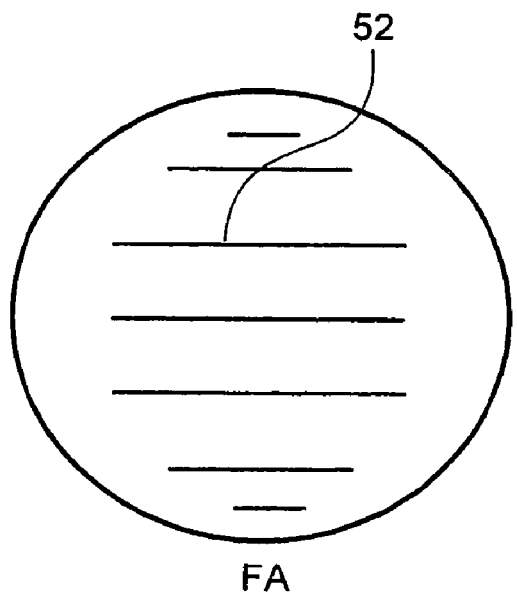

For any coherent light (light having the coherence) such as a laser beam, σ (depending on an image size of a light source on the pupil) is zero. This is because, for coherent light, an image of the light source is a point, and therefore an image on the pupil is also a point. It goes without saying that, as shown in FIG. 5(a), using a different lens system, an enlarged beam of light 51 is made to project on the pupil. However, since a laser beam has coherence, there is obtained a similar result 52 as is obtained for a case where all of the beam goes out of a point where σ=0, accordingly the problem cannot be solved. Therefore, means for reducing the coherence of a laser beam is a prerequisite. Reducing the coherence requires reduction of either the temporal coherence or the spatial coherence.

Figure 6A:
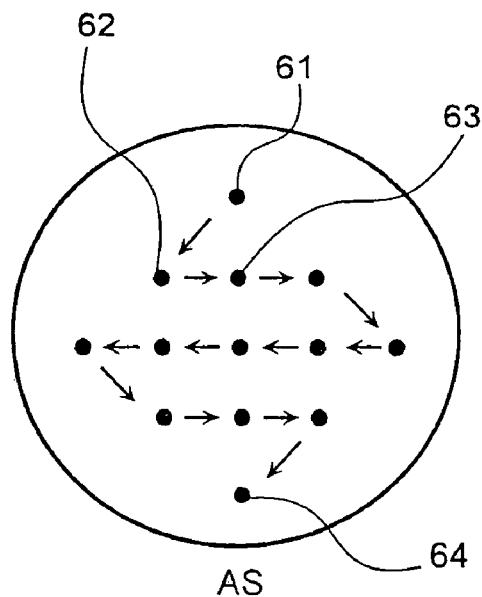
FIGS. 6(a) and 6(b) are diagrams showing illumination conditions on the pupil of the detecting objective lens and FIGS. 6(c) and 6(d) are diagrams showing the illumination conditions in the field of view, respectively, both produced by laser beam illumination according to the present invention.
Figure 6C:
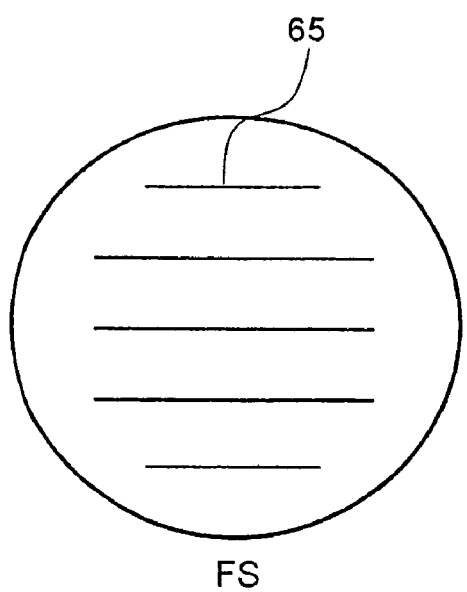

In view of this, the present invention proposes a method wherein firstly, an image of the light source is formed on the pupil of the objective lens of the detecting equipment, and then the image is illuminated on the sample through the objective lens in such a manner, for example, that first a point 61 in FIG. 6(a) is illuminated, along with a second point 62, a third point 63, . . . to achieve substantial illumination 65 all over the field of view, as seen in FIG. 6(c). During this process, the speckle pattern and an image of the overshoot and undershoot can be obtained at each location, but respective images are not coherent to one another because these were obtained at different times. Therefore, if these images are summed up on the detector, the same image can be obtained as is obtained by an incoherent light source. To perform the summation on the detector, a storage-type detector such as the CCD image sensor is suitable.

Figure 6B:
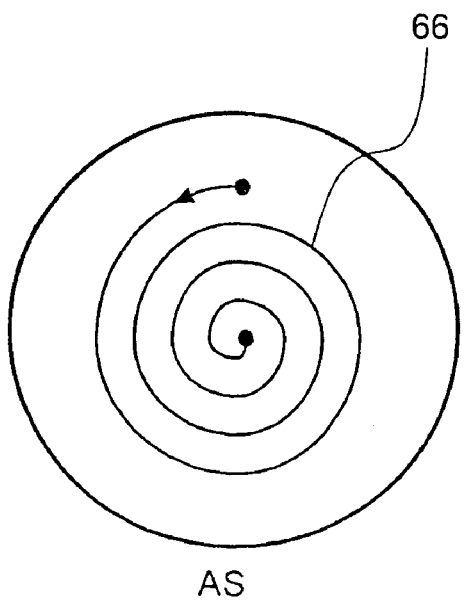
Figure 6D:
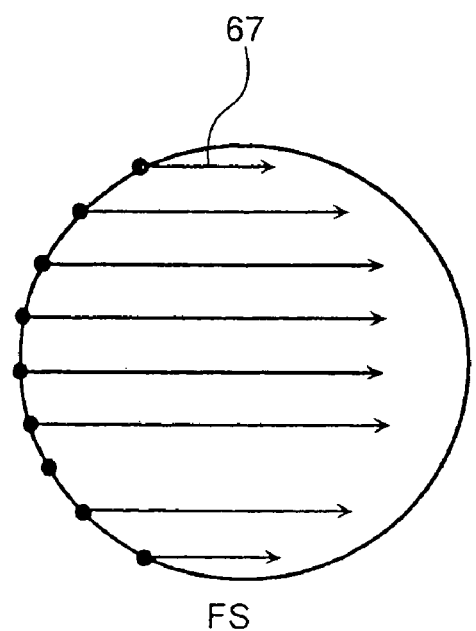

In this case, a scanning scheme may be spiral scanning 66, as seen in FIG. 6(b), and television-like (raster) scanning 67, as shown in FIG. 6(d), and any other scanning may be employed, as long as the whole field of view is scanned. However, it goes without saying that the scanning should be completed within a storage time of the detector. Therefore, it is recommended that the scanning should be performed in synchronization with operation of the detector.

In this way, an image by illumination 65 covering the whole field of view as shown by FS in FIG. 6(c) can be obtained.

Further, although not shown in the drawings, the same effect as that of this scheme can be obtained through the steps of: making up a secondary light source consisting of a plurality of point light sources by inserting a fly-eye lens in an optical path of a UV laser beam emitted from a laser source; forming an image of this secondary light source consisting of a plurality of the point light sources on the pupil of the above-described-objective lens; and varying a position of this image of the secondary light source temporarily on the pupil of the objective lens.

Figure 7:
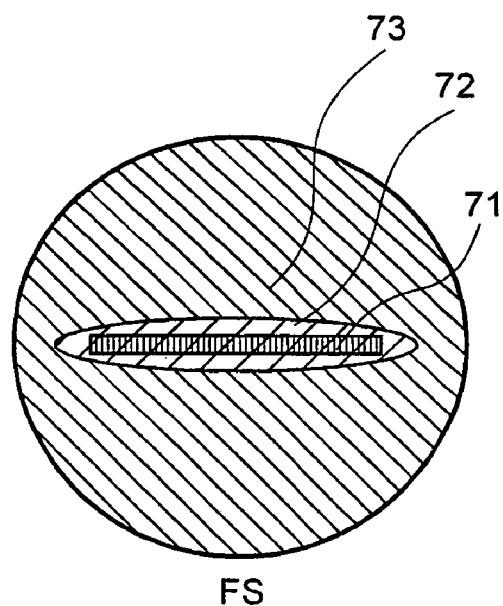
FIG. 7 is a diagram showing a relationship between a CCD image sensor detector and an illuminated region in the field of view.
Figure 8:
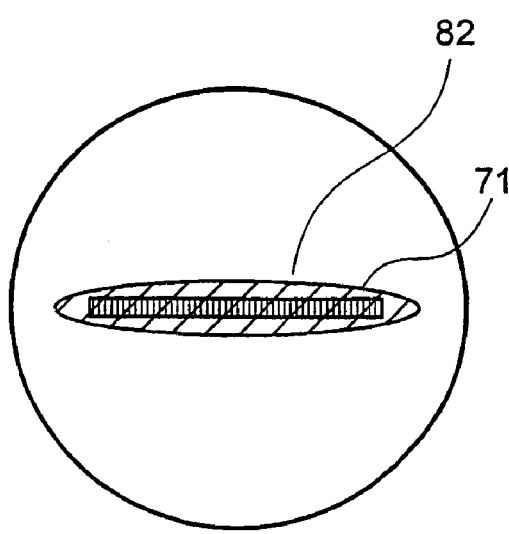
FIG. 8 is a diagram showing a relationship between the CCD image sensor detector and the illuminated region in the field of view to improve the illuminance.

Here, a case will be considered where a one-dimensional image sensor (for example, a solid state imager such as the CCD image sensor etc.) is used that is a storage-type detector and that is advantageous in effecting rapid scanning of the test sample in the whole area of a narrow field of view such as that of a microscope. As shown in FIG. 7, when the whole area of the field of view is illuminated for a one-dimensional image sensor 71, illumination contributing to detection is only that in area 72, whereas that in area 73 occupying a major portion of the optical power does not contribute to detection at all. To improve the illuminance, it is desirable to perform linear illumination as an area 82 to the one-dimensional image sensor 71, as shown in FIG. 8. (A two-dimensional image can be obtained by scanning the CCD image sensor in a direction perpendicular to an alignment direction of elements of a sensor array thereof.)

Figure 9A:
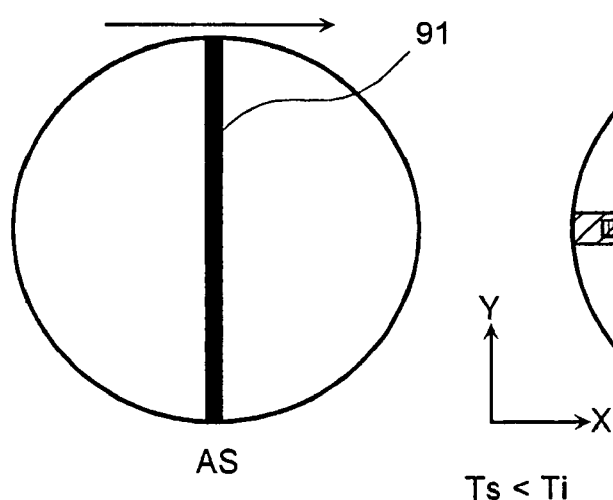
FIG. 9(a) is a diagram showing the CCD image sensor and the illumination condition on the pupil of the detecting objective lens and FIG. 9(b) is a diagram showing the illumination condition in the field of view, both produced by laser beam illumination according to the present invention.
Figure 9B:
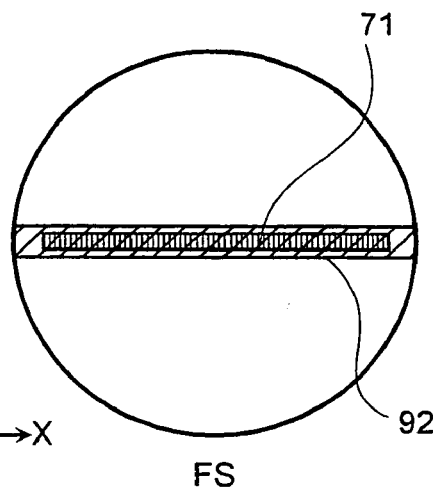
Figure 10A:
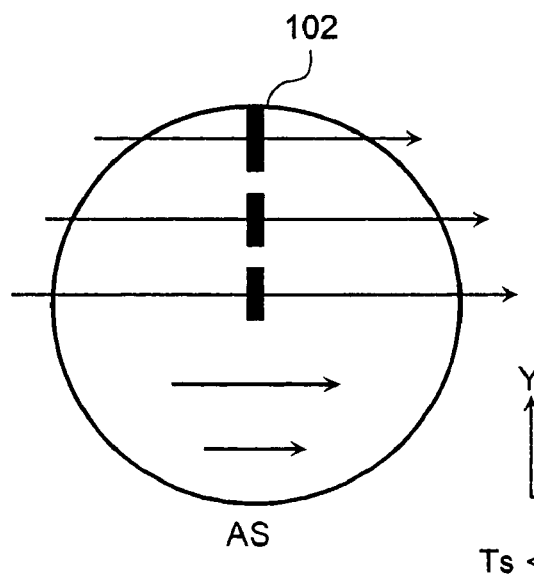
FIG. 10(a) is a diagram showing a TDI image sensor and the illumination condition on the pupil of the detecting objective lens and FIG. 10(b) is a diagram showing the illumination condition in the field of view, both produced by laser beam illumination according to the present invention.
Figure 10B:
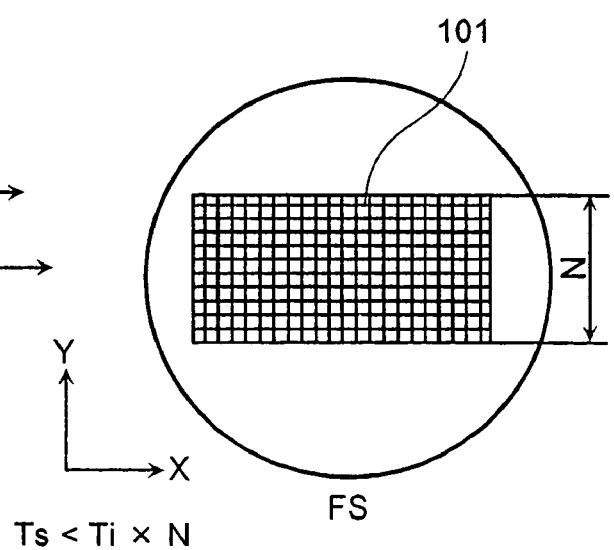

In that case, by performing illumination whose longitudinal direction is set in the Y-direction as shown in FIG. 9(a) (a longitudinal direction of an area 91 shown by a bold solid line in the figure), illumination 92 adjusted to a shape of the CCD image sensor 71 can be produced, as seen in FIG. 9(b). Also, the scanning on the pupil is performed in the X-direction. In this case, its scanning period $T_s$ should be shorter than the storage time $T_i$ of the CCD image sensor. Through this procedure, summation of images can be done. A problem associated with this scanning scheme is that, since the illumination has some spread in the Y-direction on the pupil from the beginning, it is impossible to scan in the Y-direction. Consequently, the overshoot and undershoot which occur in the Y-direction of the CCD image sensor in the field of view cannot be reduced. On the contrary, if the length of the illumination in the Y-direction is shortened with the intention to scan in the Y-direction on the pupil, the width of the illumination in the Y-direction become wider in the field of view and hence the illuminance decreases.

To solve this problem, the present invention uses a Time Delay Integration Image sensor (hereinafter referred to as a "TDI image sensor"). The TDI image sensor, which is one of the CCD image sensors, has a structure in which a plurality of one-dimensional image sensors are arranged in two dimensions and is of such a type that the amount of light is intentionally increased by delaying, by a prescribed time, an output of each one-dimensional image sensor which takes a picture at a position and then adding it to an output of an adjacent one-dimensional image sensor which takes a picture at the same position. In the case of the TDI image sensor, since N stages of the CCD image sensors (N equals a few tens to one hundred) are aligned in the field of view, even if the width of the area illuminated in the field of view is widened by N times, illumination light is utilized effectively for detection.

Because of this fact, the length of converged rays of light 102 in the Y-direction on the pupil can be reduced to approximately 1/N times the length of the case of the CCD image sensor, and the scanning can be performed both in the X-direction and in the Y-direction on the pupil. Consequently, the overshoot and undershoot occurring both in the X-direction and in the Y-direction of the TDI image sensors on the pupil can be reduced, and hence excellent detected images can be obtained.

Moreover, the scan period $T_s$ on the pupil only needs to be shorter than N times the storage time of one stage of the TDI image sensor. However, considering the illuminance distribution generated in the field of view, in order to attain substantially uniform detection, it is desirable that $T_s$ should be shorter than a half of N times $T_i$.

Moreover, to perform uniform illumination in the field of view, it is desirable that rays of light from a laser source should be converged after passing through a fly-eye lens or an integrator rather than have these rays be converged directly onto the pupil.

Figure 11:
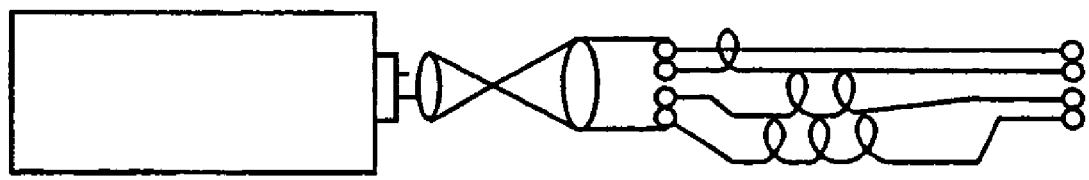
FIG. 11 through FIG. 15 are diagrams schematically showing respective contrivances that reduce the spatial coherence of laser beam illumination according to the present invention.

Next, means for reducing the spatial coherence will be described. To reduce the spatial coherence, it is only necessary to prepare a plurality of beams of light passing through optical paths whose lengths are mutually different an the amount larger than the coherence length. More specifically, if output light of a laser is made to go into a bundle of a plurality of fibers 11 or glass rods, each of which has a mutually different length, as shown in FIG. 11, output light from such a device will become incoherent light (having no coherence). If these light components are arranged on the pupil, respectively, an image free from overshoot and undershoot and speckle can be obtained.

Figure 11A:
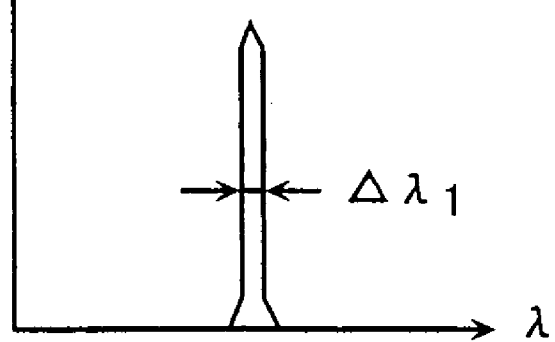
FIGS. 11(a) and 11(b) are diagrams showing examples of the oscillation spectrum of a laser beam.
Figure 11B:
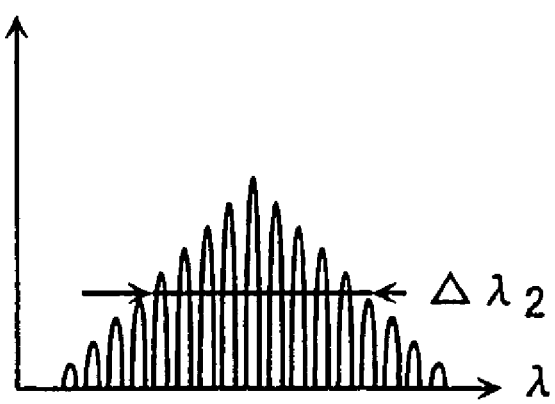
Figure 12:
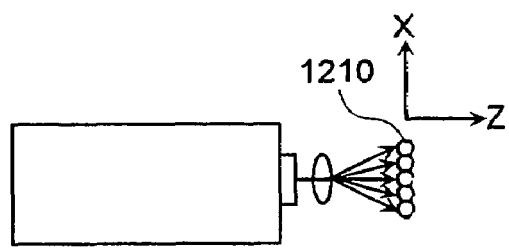
Figure 12A:
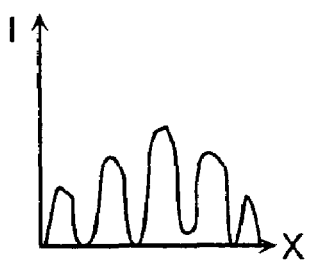
FIGS. 12(a) through 12(e) are diagrams showing different distributions of lateral modes of outgoing light from a plurality of optical fibers illuminated by a laser beam.
Figure 12B:
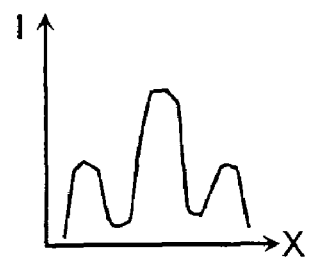
Figure 12C:
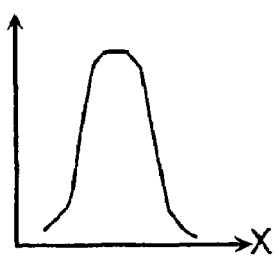
Figure 12D:
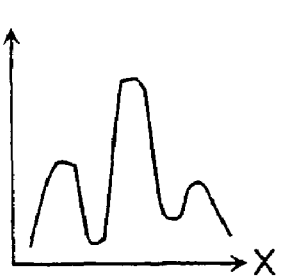
Figure 12E:
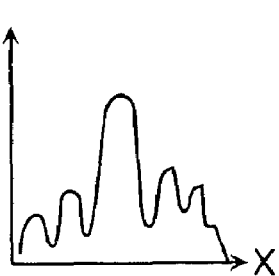

In addition, it is desirable with this scheme that the coherence length of the laser source should be shorter. For this end, a laser beam having an oscillation spectrum with a plurality of longitudinal modes and hence a wide wavelength band $\Delta\lambda_2$ of emission wavelength, as shown in FIG. 11(b), is more suitable than a laser beam having an oscillation spectrum with a single longitudinal mode and hence narrow wavelength band $\Delta\lambda_1$, as shown in FIG. 11(a).

Furthermore, regarding other contrivance for reducing the spatial coherence, there is a scheme utilizing a phenomenon that, when light is coupled to a misaligned fiber, lateral modes of outgoing light (spatial distribution and optical intensity I to a space) vary from that of a fiber with no misalignment. Normally, such variation of modes is regarded as an unfavorable phenomenon in industrial applications, and generally efforts to reduce the variation of lateral modes have been exerted. However, in accordance with the present invention, in taking advantage of this phenomenon another way, light from a laser is coupled to a plurality of fibers 1210 with their optical axes intentionally misaligned to generate outgoing light having different distributions of lateral modes, as shown in FIGS. 12(a) through 12(e). As a result, since outgoing beams of light thus obtained become mutually incoherent, these beams are arranged on the pupil.

Figure 13:
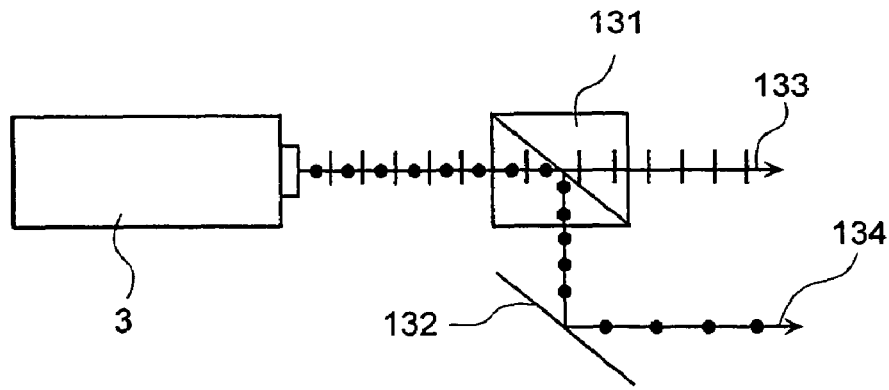

FIG. 13 is a diagram showing a condition where emitted light from a laser source 3 is divided into two beams of light 133 and 134 having polarization planes perpendicular to each other by a polarizing beam splitter 131. Numeral 132 is a mirror for deflecting the light into a different direction.

Since two beams of light having mutually perpendicular planes of polarization are mutually incoherent, beams of incoherent light can be obtained with an optical system of a very simple configuration. With this scheme, only two beams of incoherent light can be obtained. However, if this scheme is combined with already-mentioned methods, light with virtually zero coherence can be easily obtained.

Figure 14:
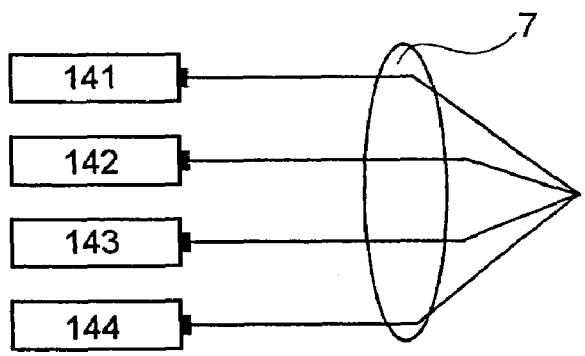

Further, since mutually independent light sources are incoherent, independent light sources 141, 142, 143, 144, . . . may be used, as they are, to illuminate respective points on the pupil of the objective lens 7, as shown in FIG. 14.

Figure 15:
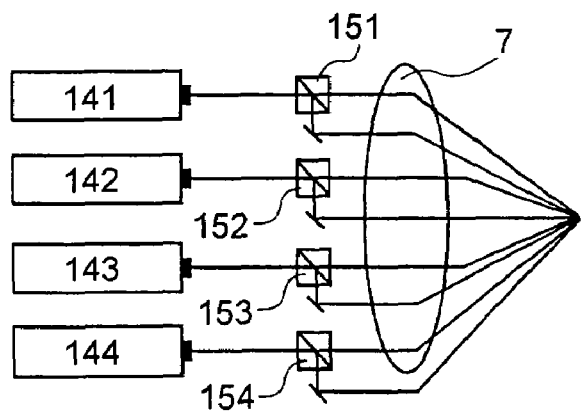

Furthermore, if this method is used in conjunction with the aforesaid method with the polarizing beam splitter, an effect that laser sources are substantially doubled in number can be obtained, as shown in FIG. 15. Moreover, if the number of beams is maintained to the same as before, the number of laser sources can be reduced to one-half, and hence the cost can be held down.

In the foregoing, a plurality of means for reducing the coherence of a UV laser beam, illuminating 4 plurality of points on the pupil with this UV laser beam with reduced coherence, and obtaining an image by converging rays of light with the objective lens have been described. Each of these means can be used jointly with other means. Moreover, any other means for reducing the coherence equivalent to these means may be used.

Moreover, although not shown in the drawings, a scheme where a diffuser is inserted on the way of an optical path of a UV laser beam and this diffuser is rotated or reciprocated may be used to reduce both the spatial coherence and the temporal coherence of the UV laser beam at the same time. Further, this diffuser can be used in conjunction with other coherence reducing means mentioned above.

Figure 16:
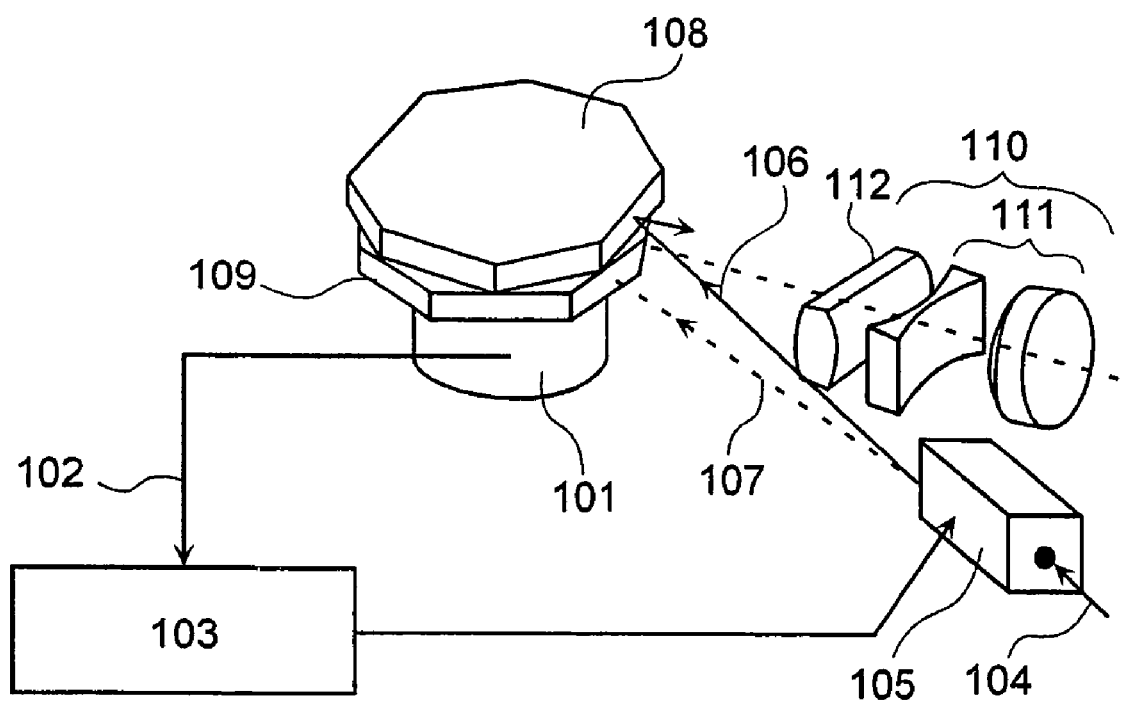
FIG. 16 is a diagram showing a first embodiment of a laser beam scanning mechanism according to the present invention.

As a scanning mechanism 4 of a laser beam indicated in FIG. 1, an arrangement shown in FIG. 16 through FIG. 28, which will be described below, may be adopted. Firstly, referring to FIG. 16, a first embodiment of the laser beam scanning mechanism according to the present invention will be described. That is, in the first embodiment, polygon mirrors 108 and 109 are stacked up with a rotation phase difference of half the period between respective mirror facets thereof being set and the stack thus made is configured to be rotatable by a rotating motor 101. The polygon mirrors 108 and 109 are mirrors of mutually identical shape and their effective scanning time ratio is approximately 50%. Here, the unavailable time is defined as a time when a laser beam hits an edge part of each mirror facet of the polygon mirror and thereby specula reflection cannot be exerted, whereas the available time is defined as a time when the laser beam hits a flat plane to exert specula reflection. The available scanning time ratio is given by the ratio of the available scanning time to the total time. Further, each polygon mirror is fixed on a spindle of the rotating motor 101 in such a manner that mirror facets comprising one polygon mirror are set with a rotational phase of half the period shifted to corresponding mirror facets comprising the other polygon mirror.

At the same time, each of these polygon mirrors 108 and 109 are irradiated with a laser beam 104 from a laser source (not shown in the drawings) through an A/O modulator 105. An A/O modulator 105 switches the laser beam into either of irradiation paths 106 and 107 based on a control signal generated by a rotation position-mirror switching signal converter 103 from an output 102 transmitted from an encoder attached to the rotating motor 101. In case two polygon mirrors are switched over, if first order light (for example, light 107) and zero-th order light (for example, light 106) from the A/O modulator 105 are used, the switching can be done using only the single A/O modulator 105, and this is convenient. It should be understood that since just switching an optical path is needed, any means other than A/O modulators may be used. That is, during the available scanning time of the polygon mirror 109, the optical path in use is switched to the optical path 107, and during the unavailable scanning time of the polygon mirror 109, the optical path in use is switched to the path 106. By this scheme, the available scanning time ratio of this polygon mirror system reaches approximately 100%.

Therefore, even when a laser other than an easy-to-modulate semiconductor laser is used along with a polygon mirror which has a high scanning speed and hence a low available scanning time ratio of about 50%, highly-efficient and high-speed scanning of a laser beam can be performed.

If the number of stages of polygon mirrors to be stacked is increased, this scheme can be applied to a polygon mirror whose available scanning time ratio is shorter than 50%. In this case, two or more polygon mirrors are stacked up in such a way that the mirror facets comprising each polygon mirror are shifted by one n-th times the period (where n denotes the number of the polygon mirrors) with respect to mirror facets of other polygon mirrors.

By the way, in this configuration there is an optical system (for example, a lens system) 110 having both: a function of a lens system 112 capable of scanning two laser beams, which are reflected from the polygon mirrors 108 and 109, respectively, along with the same scanning line on an object (in case such a defect as minute foreign particles, a minute pattern defect, etc. is examined, the object will be a test object); and a function of a F-θ lens 111 capable of scanning both laser beams with the same scanning speed.

Figure 17A:
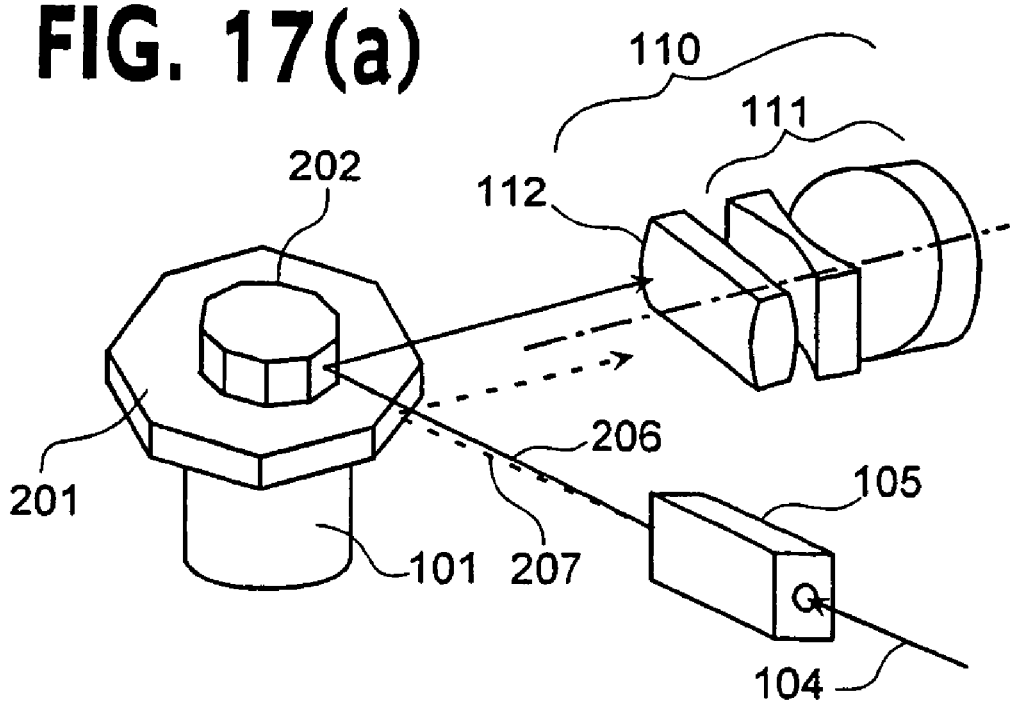
FIG. 17(a) is a diagram showing a second embodiment of the laser beam scanning mechanism according to the present invention.

Next, referring to FIG. 17(a), a second embodiment of the laser beam scanning mechanism according to the present invention will be described. The second embodiment comprises, as shown in FIG. 17(a), a polygon mirror 201 and a polygon mirror 202 which have different numbers of mirror facets relative to each other and are stacked up. Because of this configuration, each scanning angle range (i. e. angle range in which reflected light is scanned), which is inversely proportional to the number of mirror facets, is different from that of the other polygon mirror. However, the diameters of the polygon mirrors 201 and 202 are determined so that a period of time required for each angle range to be scanned is the same.

Figure 17B:
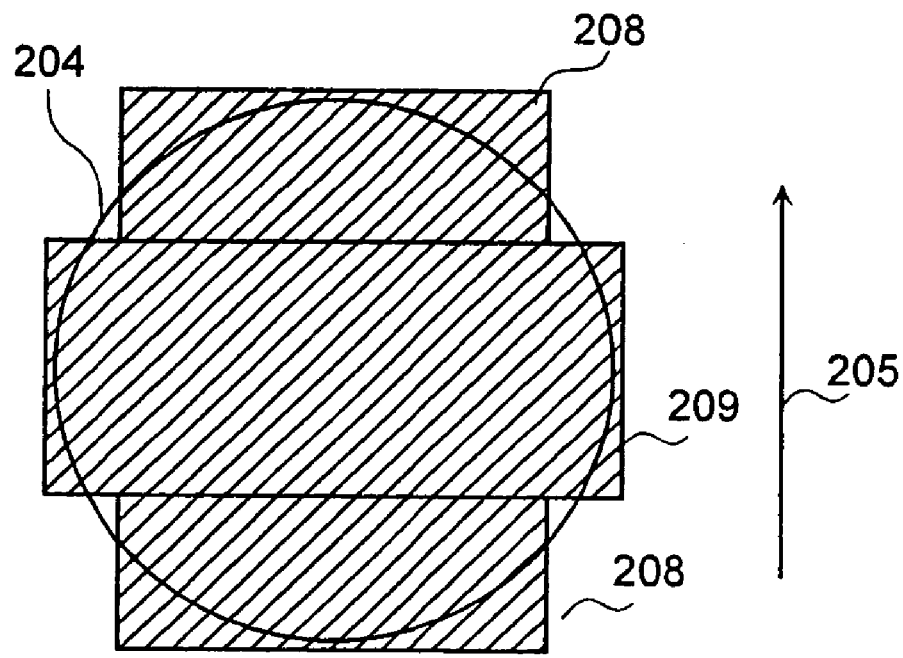
FIG. 17(b) is a diagrammatic top plan view of an object being scanned by the mechanism of FIG. 17(a).

This configuration provides a scanning scheme, in case the object 204 having a circular shape, for example a semiconductor wafer, is moved in a direction indicated by an arrow 205 in FIG. 17(b) (on the plane of the figure) and the scanning is performed with polygon mirrors in a direction perpendicular to the direction of the arrow, wherein, in a section 208 where a small scanning angle is sufficient, the A/O modulator 105 scans, for example, the zero-th order diffraction light 206 using the polygon mirror 202, whereas, in a section 209 where a large scanning angle is necessary, the A/O modulator 105 scans, for example, the first order diffraction light 207 instead using the polygon mirror 201, as shown in FIG. 17(b).

With the use of this second configuration, the time necessary to scan the whole surface of the object 204 can be reduced compared to that of a configuration wherein the scanning is performed with the same scanning angle which is only suitable for the area 209.

Here, a configuration using two kinds of polygon mirrors has been described. However, it is well understood that if more kinds of mirrors are used, highly-sophisticated illumination with higher efficiency can be performed. Moreover, since the timing necessary for switching each polygon mirror is not so delicate, it is not necessary to detect the angle from an encoder attached to the rotating motor 101 and to rotate polygon mirrors synchronously. Thus, polygon mirrors 201 and 202 may be rotated using respective motors.

By the way, also in this second configuration, there is an optical system (for example, a lens system) 110 having both: a function of a lens system 112 capable of illuminating the same scanning line on the object (in case a defect such as minute foreign particles, a minute pattern defect, etc. is examined, the object will be a test object) with a laser beam reflected by either of the polygon mirrors 201 and 202; and a function of the F-θ lens 111 capable of scanning with an identical scanning speed.

Figure 18A:
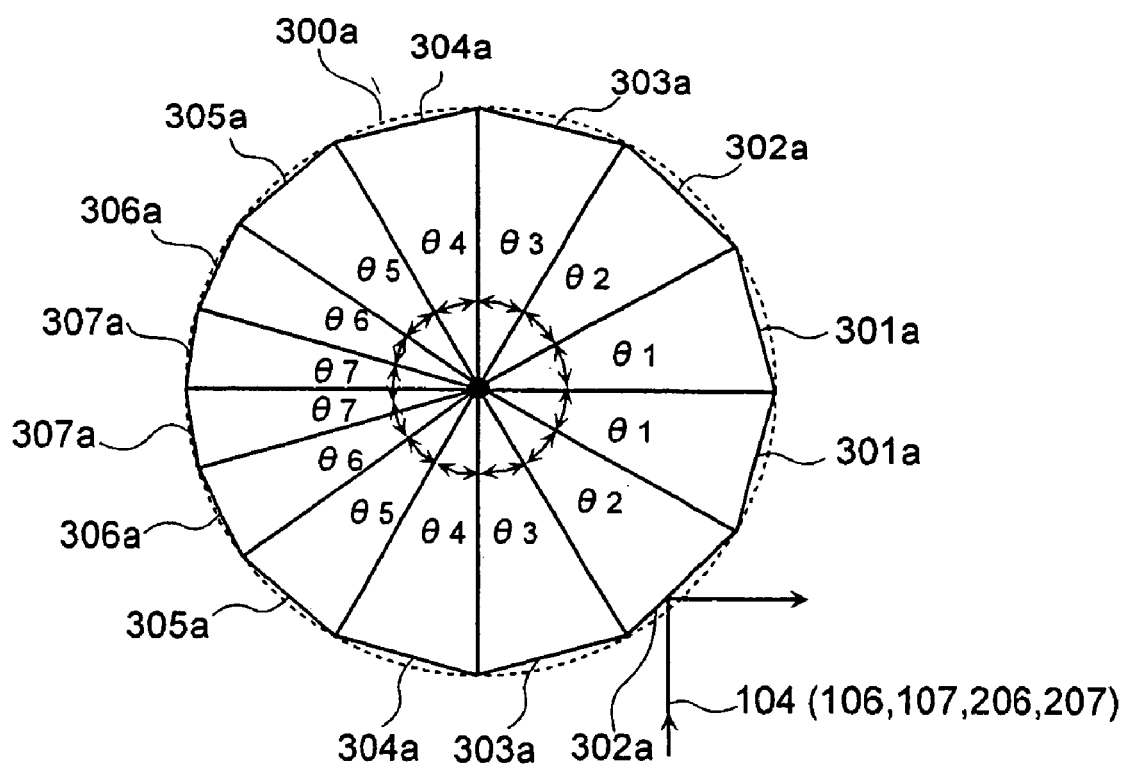
FIG. 18(a) is a diagram showing a third embodiment of the laser beam scanning mechanism according to the present invention.

Next, referring to FIG. 18(a), FIG. 18(b) and FIG. 19, a third embodiment of the laser beam scanning mechanism according to the present invention will be described. By the way, in case the scan object 204 of a laser beam has a circular shape, such as a semiconductor wafer, if a laser beam is scanned simply over a rectangular area circumscribing the circle with respect to the scanned object 204, the laser beam inevitably will scan outside of the object area and hence the efficiency of irradiation goes down. In view of this fact, this third embodiment adopts a polygon mirror 300a, as shown in FIG. 18(a), which is a top view of the polygon mirror 300a), wherein angles θ7 to θ1 and θ1 to θ7 subtended by respective mirror facets 307a to 301a and 301a to 307a (namely, lengths of mirror facets along its circumference) are varied, respectively, and hence the scanning range (scanning length) on the object L7 to L1 and L1 to L7 can be varied when the laser beam 104 (106, 107; 206, 207) is reflected.

Figure 18B:
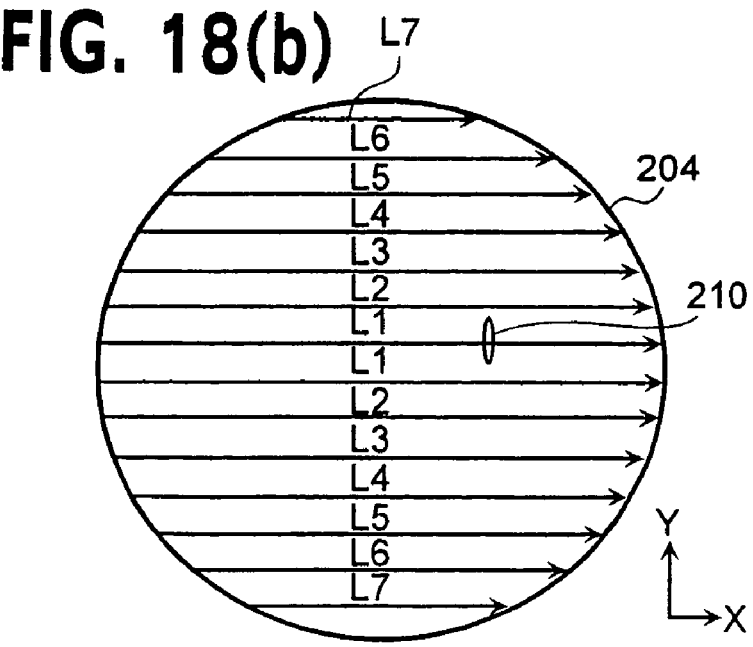
FIG. 18(b) is a diagrammatic top plan view of a wafer scanned by a laser beam scanning mechanism.

By the way, in case a laser beam 210 of, for example, a slit shape or spot shape is scanned, as indicated by L7 to L1 and L1 to L7, over the scan object 204 of circular shape, such as a semiconductor wafer, as shown in FIG. 18(b), since it is generally necessary to scan the object along equally spaced lines in the Y-direction, a subtended angle by each mirror facet can be determined in such a manner that the object of a circular shape is scanned over its whole surface while the polygon mirror is rotated at least one revolution, even if a stage (not shown in the drawings) on which the object 204 is mounted is translated intermittently in the Y-direction. By the way, if the laser beam 210 is shaped in a slit form, a linear image sensor composed of a CCD image sensor, or a TDI image sensor, or the like can be used as a detector.

Figure 19:
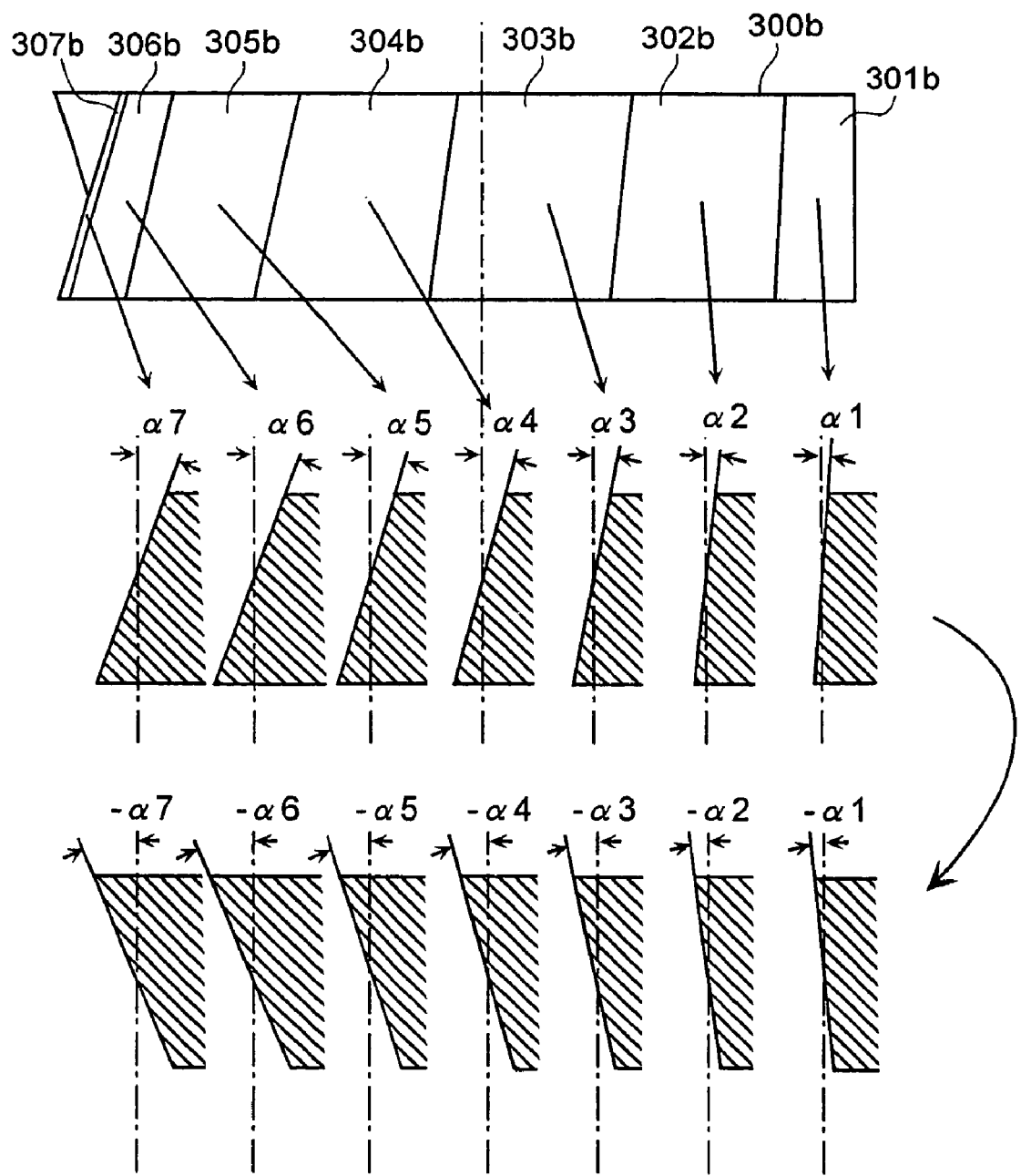
FIG. 19 is a diagram illustrating a configuration of an irregular-type polygon mirror employed in the third embodiment.

Moreover, as shown in FIG. 19, a polygon mirror 300b may be configured so that mirror facets 307b to 301b and 301b to 307b have different inclined angles α7 to α1 and α1 to α7, which are varied gradually, with respect to a rotation axis, and hence, for example, the slit-like or spot-like laser beam 210 can be scanned two-dimensionally over the object 204 of circular shape, as shown in FIG. 18(b). Further, numerals L1 to L7 indicate scanning lines produced by mirror facets 301b to 307b in FIG. 18(b).

Therefore, in the case of the polygon mirror 300b, it is not necessary to translate a stage with the object 204 of circular shape mounted on it in the Y-direction. However, when the object 204 is irradiated with the laser beam 210, positing of the laser beam 210 is necessary.

In addition, this third embodiment can be applied to either of the above-described first and second embodiments.

Figure 20:
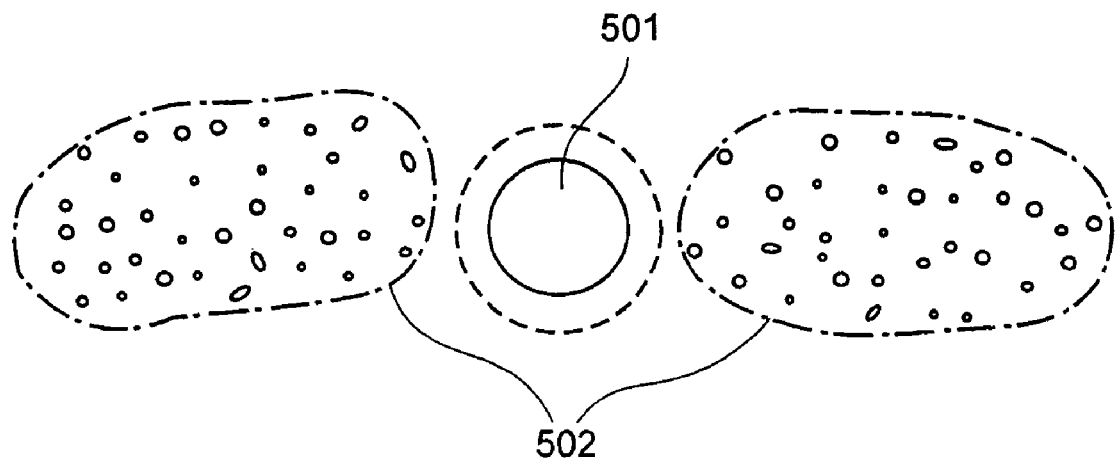
FIG. 20 is a diagram illustrating a condition of the light reflected from the polygon mirror.
Figure 21:
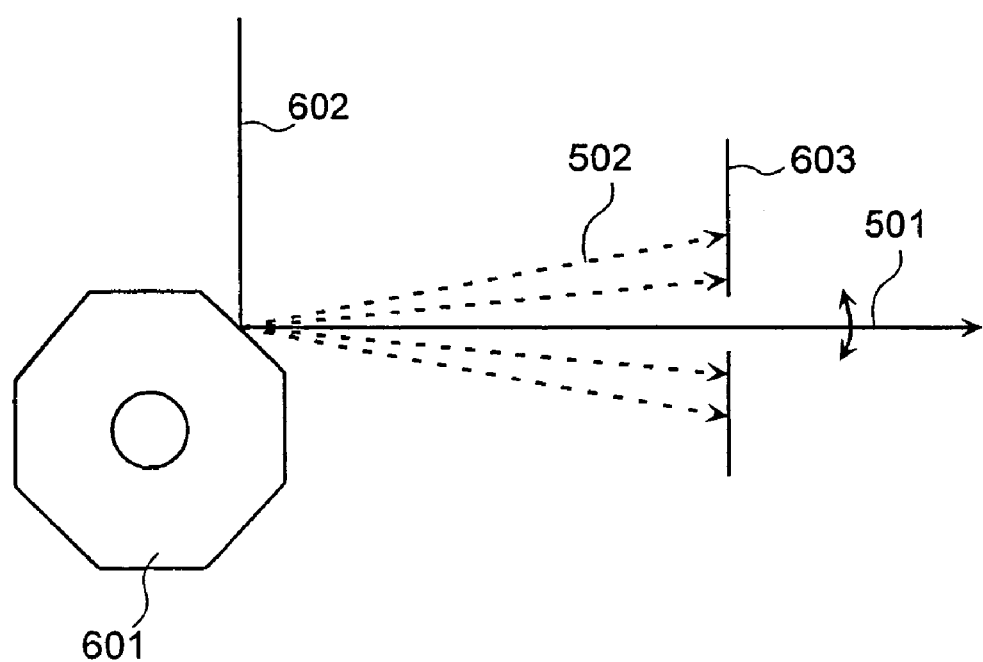
FIG. 21 is a diagram showing a fourth embodiment of the laser beam scanning mechanism according to the present invention.

Next, referring to FIG. 20 and FIG. 21, a fourth embodiment of the laser beam scanning mechanism according to the present invention will be described. A polygon mirror 601, as shown in FIG. 21, is manufactured by cutting a block of aluminum, its alloy, or beryllium. Mirror facets of the polygon mirror 601 thus manufactured are occasionally of insufficient profile irregularity (plane roughness) when being irradiated with a laser beam 602 whose wavelength is not longer than that of ultraviolet rays. FIG. 20 is an illustration showing a reflected beam in this case projected on a screen. As shown in FIG. 20, when the profile irregularity of the mirror facet is insufficient, there occurs scattered light 502 in the periphery of a specula reflection beam of light 501 from the mirror facet. An experiment carried out by the inventors has revealed that when the plane-roughness of the mirror facet is controlled to be equal to 50A or less, the amount of scattered light 502, namely the fraction of the light lost, is reduced to 5% or less of the total amount of reflected light.

Since the scattered light 502 deteriorates the beam quality, it is desirable to remove it as much as possible. In view of this, a fourth embodiment is configured so as to remove the scattered light 502 by providing a scattered light trap 603, for example, a plate with a hole through which only the specula reflection beam 501 passes. In this way, by providing the scattered light trap 603, the quality of the scanning laser beam can be improved by removing the component of the scattered-light 502 not only in the case of a surface roughness of more than 50A, but also in the case of surface roughness of not more than 50A.

By the way, the larger the clearance between the mirror facet of the polygon mirror and the scattered light trap 603, the better will be the performance in trapping the scattered light 502. An experiment carried out by the inventors has revealed that a clearance of about 1 m can give a satisfactory trapping performance.

The fourth embodiment described above can also be applied to either of the above-described first, second, and third embodiments.

Next, referring to FIG. 22 to FIG. 24, a fifth embodiment of the laser beam scanning mechanism according to the present invention will be described. The fifth embodiment is constructed basically using a galvano mirror. Ordinary galvano mirrors can only perform a slow scanning with a scanning frequency in the range of up to a few hundreds Hz at best. However, a resonant-type galvano mirror, which is also called as a resonant galvano mirror, can perform a scanning in the range of a few kHz or more, but reportedly, the driving signal must consist only of sinusoidal waves. Therefore, the scan angle varies sinusoidally and the scanning speed of the beam cannot be constant.

Accordingly, when the laser beam 104 is scanned over the object 204 mounted on the stage 130 using a resonant-type galvano mirror, called a resonant galvano mirror, and an image signal is obtained from an image of the object 204 by using a sensor, especially a storage-type sensor, for example a TDI image sensor, the intensity of the image signal from an area being slowly scanned is relatively large, whereas that from an area being fast scanned is relatively small, because of the varying scanning speed of the laser beam.

Figure 22:
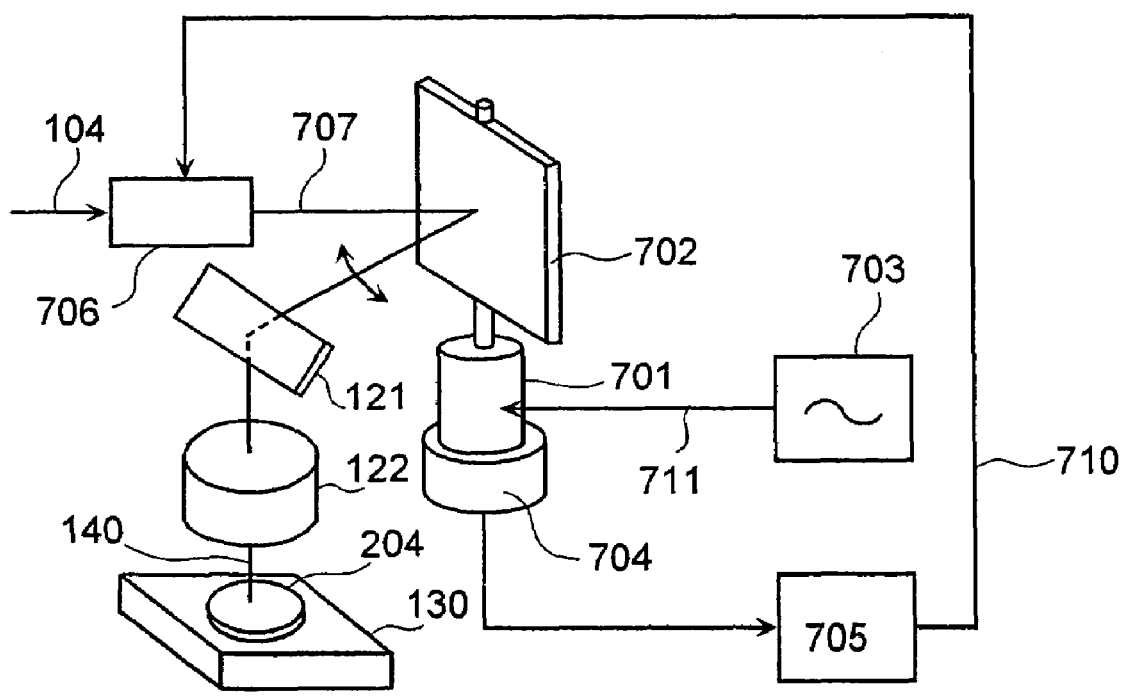
FIG. 22 is a diagram showing a fifth embodiment of the laser beam scanning mechanism according to the present invention.

In view of this, the fifth embodiment, as shown in FIG. 22, has a construction comprising a resonant-type galvano mirror (resonance operation-type mirror scanner), which is also called a resonant galvano mirror, wherein a scanning mirror 702 is driven by an actuator 701 based on a sinusoidal driving signal 711 obtained from a sinusoidal signal source 703, and a computer 705 reads the direction of the mirror from an encoder 704 attached to the actuator 701, finds the scanning speed at the point where the scanning angle is read from the scanning angle thus read, and generates a control signal.

Further, the computer 705 controls an A/O modulator 706 based on a control signal 710 indicating the scanning speed. Specifically, when the scanning is slow, the transmittance is decreased in proportion to it, whereas when the scanning is fast, the transmittance is increased, so that the quantity of light of a laser beam 707 which is made to hit the mirror 702 is being varied. As a result, even if the scanning speed of the laser beam wherewith the object 204 is irradiated varies, the object mounted on the stage 130 is irradiated with the laser beam 140 with an intensity corresponding to the scanning speed and hence the intensity of an image obtained from the object 204 becomes constant, accordingly, the value of the detected signal (image signal) becomes constant when detected by a detector 801, for example, a storage-type sensor, as shown in FIG. 23. By the way, numeral 121 denotes a half mirror and numeral 122 denotes an objective lens.

Moreover, control of the laser beam using the A/O modulator 706 may be provided after the reflection rather than before the reflection. However, in the case of after-reflection scanning, a laser beam is scanned instead.

Figure 23:
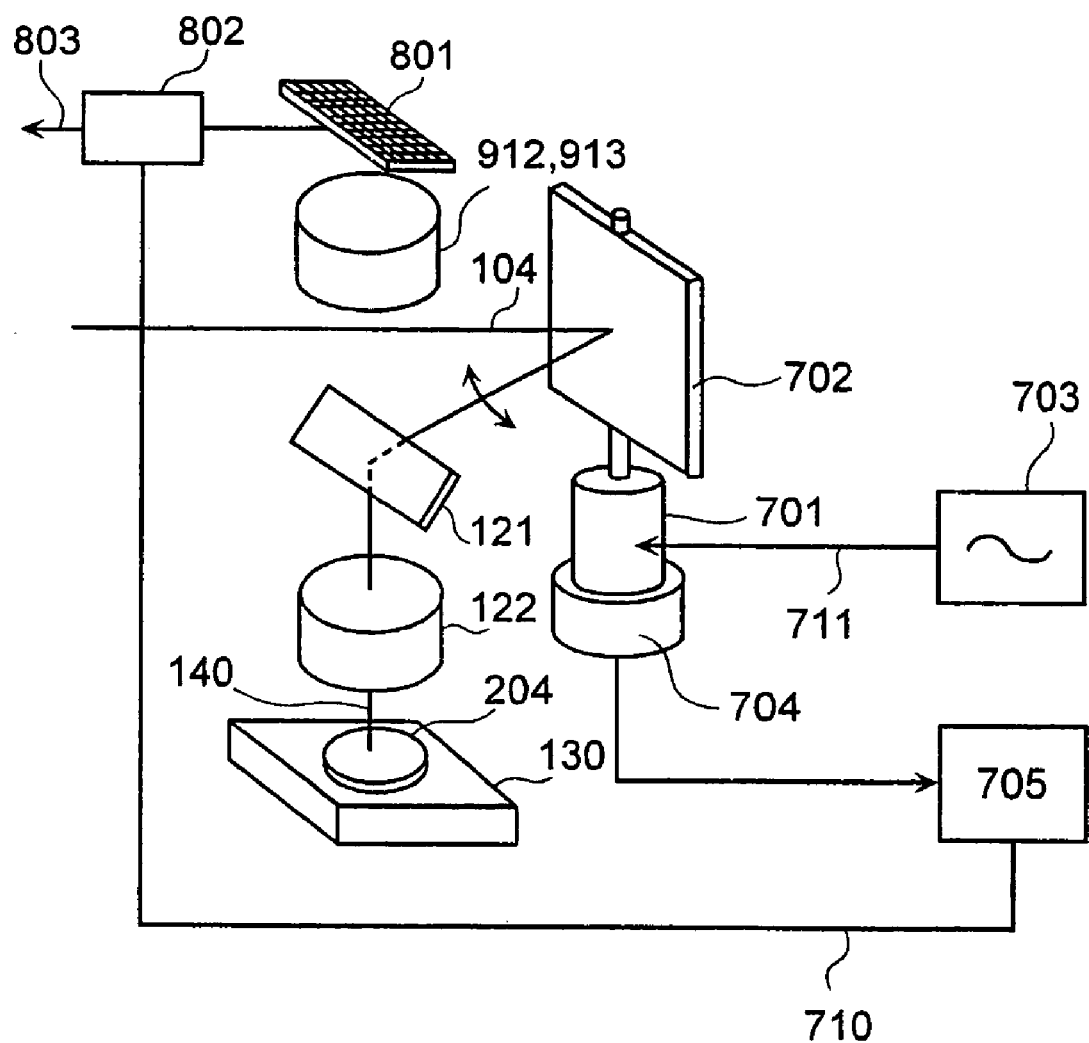
FIG. 23 and FIG. 24 are diagrams showing a variant and another variant of the fifth embodiment of the laser beam scanning mechanism according to the present invention, respectively.

Moreover, in the fifth embodiment, as shown in FIG. 23, means to change the amplification ratio in order to control the signal (image signal) detected by the detector 801, based on the control signal 710 indicating the scanning speed which is outputted from the computer 705, can give a detected signal (image signal) 803 having a constant strength even when the scanning speed of the laser beam 140 with which the object 204 is irradiated varies.

Further, in the configuration shown in FIG. 23, the A/O modulator 706 is assumed to be used in a configuration as shown in FIG. 22, and therefore description of the A/O modulator 706 is omitted. However, other modulating means capable of controlling the intensity of the laser beam in response to the scanning speed may be used without the use of the A/O modulator 706 even when the scanning speed of the laser beam with which the object 204 is irradiated varies.

Figure 24:
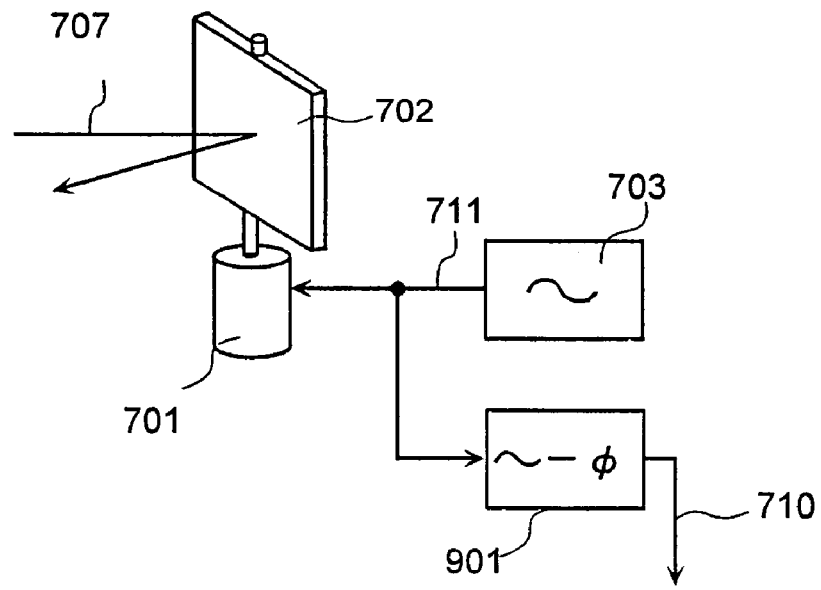

Moreover, since the direction of the mirror 702 varies with a constant phase delay with respect to the sinusoidal driving signal 711 supplied from the driving signal source 703, the control signal 710 to be used for controlling the above-described transmittance and amplification factor may be a control signal from a computer 901, which performs a calculation so as to give a phase difference to the driving signal 711 itself, as shown in FIG. 24, rather than an output from the encoder 704, as shown in FIG. 22 and FIG. 23.

The fifth embodiment described above is a scheme for keeping the detected output constant electrically, and hence this method basically introduces a loss and reduces the efficiency. Therefore, it is desirable to realize the scanning with a constant speed optically.

Figure 25:
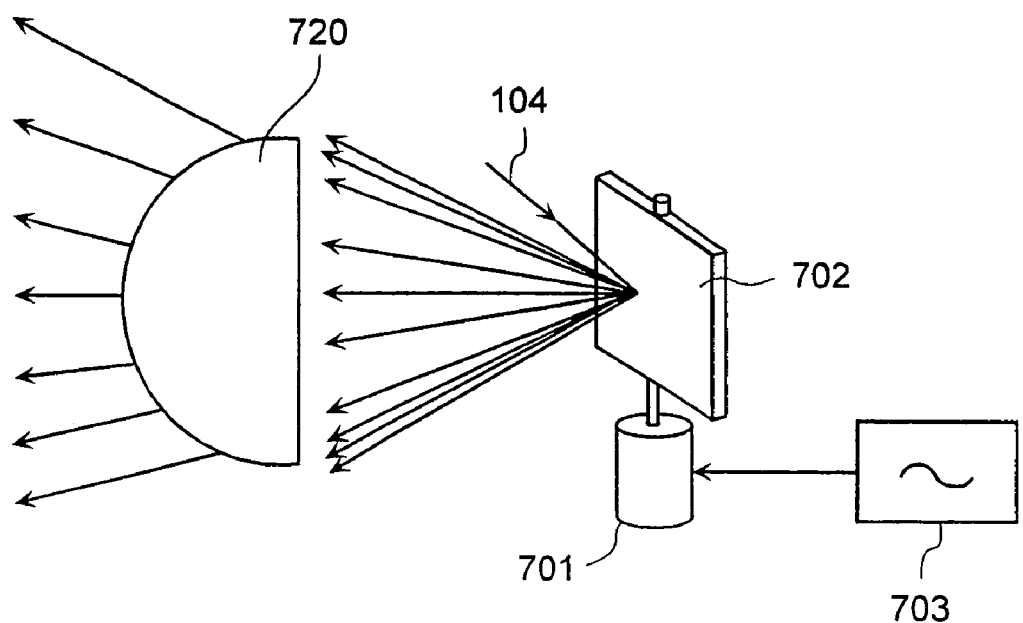
FIG. 25 is a diagram showing a sixth embodiment of the laser beam scanning mechanism according to the present invention.

Next, referring FIG. 25 to FIG. 27, a sixth embodiment of the laser scanning mechanism according to the present invention will be described. The sixth embodiment in FIG. 25 represents a case where a lens-like optical element 720 is used. In the resonant scanner 701 (i.e. resonant operation-type mirror scanner), a beam after reflection has a slow scanning speed (i.e. the variation of the deflection angle per unit time is small) at an angular position giving a large deflection angle, whereas the beam has a fast scanning speed (i.e. the variation of the deflection angle per unit time is large) at an angular position giving a small deflection angle. In view of this, a curved surface of the lens-like optical element 720 is formed so as to have a larger curvature with increasing distance from the center so that at an angular position giving a larger deflection angle, the defection angle becomes even larger according to the deflection angle.

Figure 26:
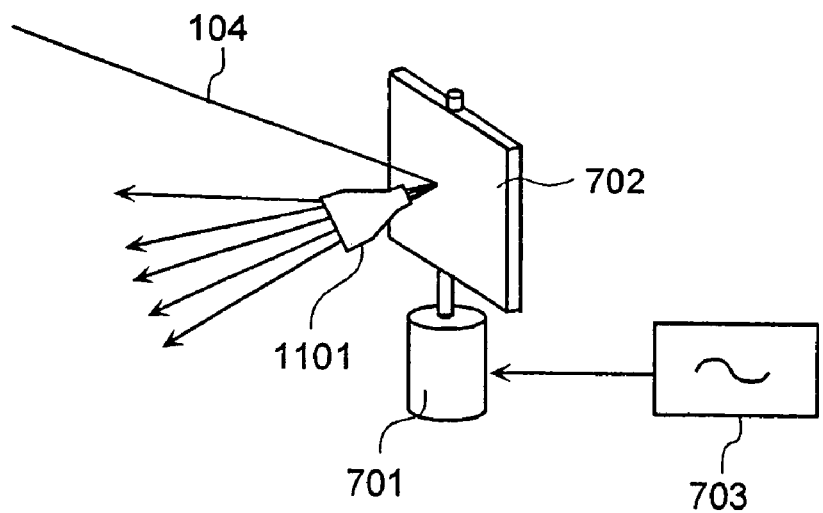
FIG. 26 and FIG. 27 are diagrams showing a variant and another variant of the sixth embodiment, respectively.

The sixth embodiment shown in FIG. 26 represents a case where the reflection direction is modified using a fiber 1101 in place of the lens-like optical element 720. In this fiber bundle 1101, the outer fibers have a larger degree of outward inclination to make a larger angle of deflection, in accordance with the position of the fiber on the exit side thereof, than an inner fiber.

Figure 27:
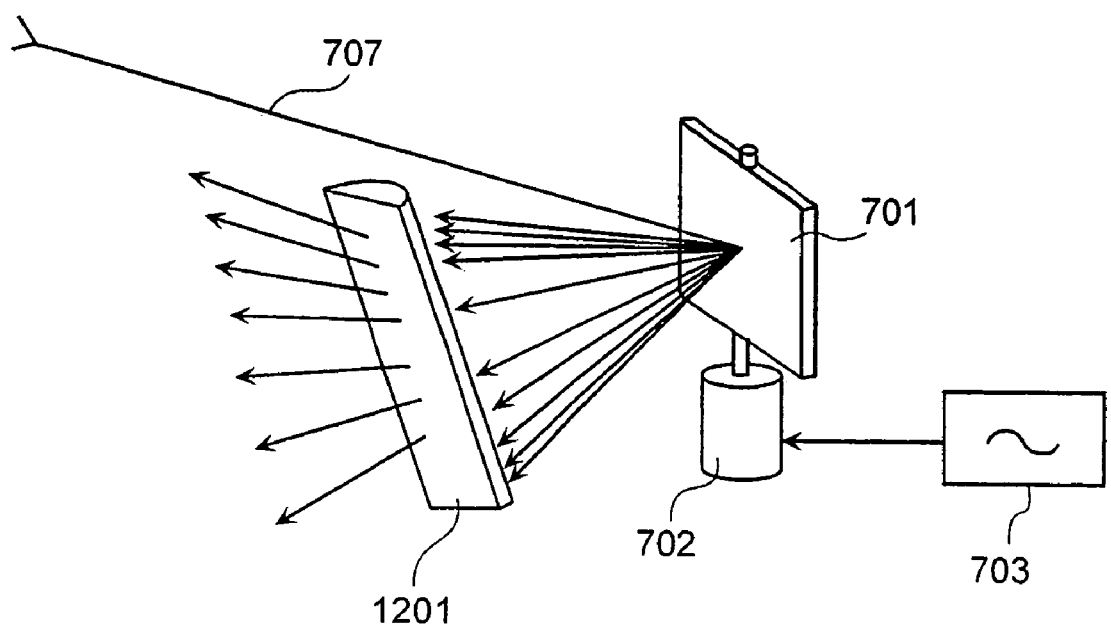

In the embodiment of FIG. 27, the reflection direction is modified to convert the direction using a holographic plate (or a deflective element) 1201 instead of the lens-like optical element 720. This holographic plate 1201 is formed so as to have a grating whose spacing becomes narrower with increasing distance from the center SO that the outgoing beam from the mirror which has passed through the holographic plate 1201 at a position nearer to its periphery suffers a larger deflection.

The foregoing is a description of various embodiments which employ a resonant galvano mirror. However, these embodiments can be constructed with any other resonant operation-type mirrors.

As described above, A/O deflectors can generate only a small amount of scanning angle, but their high-speed scanning capability and ease of control remain attractive as before. In case such an A/O defector is used, to attain a necessary scanning range with a minute scanning angle, it is necessary to secure a long optical path after the light goes out. However, when the long optical path is provided in air, the beam position and beam quality may deteriorate due to environmental changes, such as fluctuation of the air in the optical path, etc.

Figure 28:
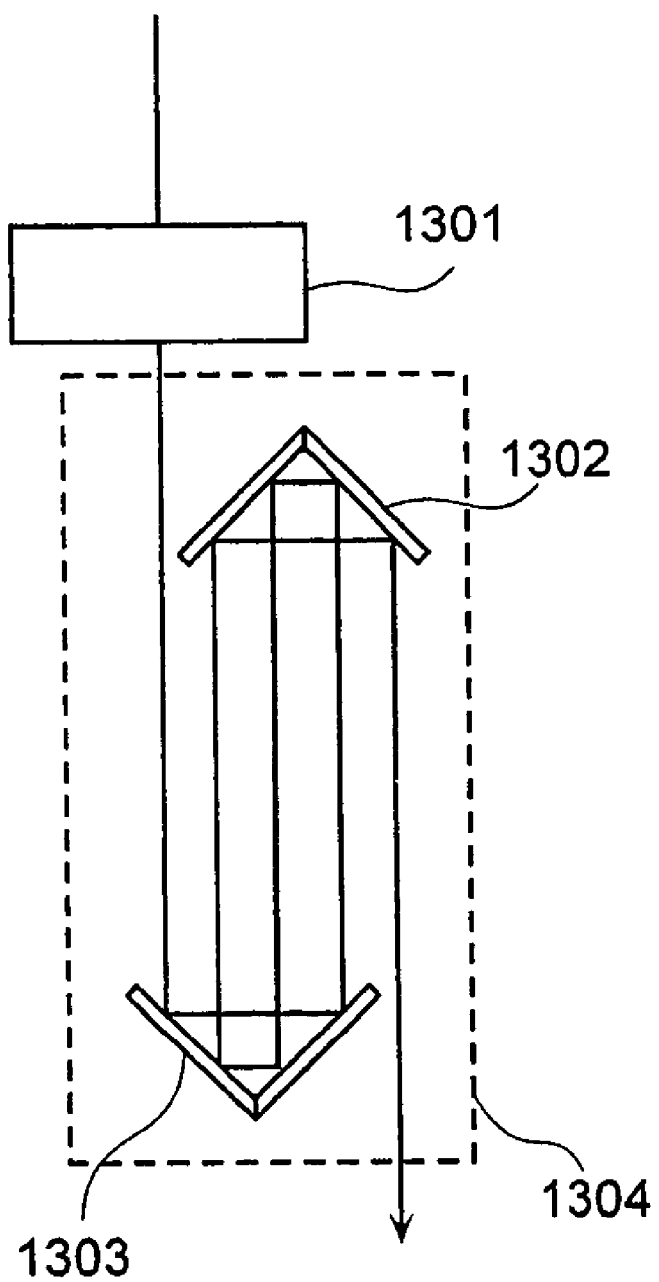
FIG. 28 is a diagram showing another embodiment of the laser beam scanning mechanism according to the present invention.

To circumvent this, as shown in FIG. 28, the optical path of the beam after leaving the A/O deflector 1301 is folded in a compact space multiple times using folding mirrors 1302 and 1303, and the space is sealed from the outside to construct a folding optics unit. By isolating this unit thermally from the outside using an insulating material and providing a heater for keeping the unit at a temperature higher than the outer environment, etc., problems of fluctuation in air and thermal deformation of optical components used are evaded, providing an optical path which makes it possible to obtain a necessary scanning range securely.

As described in the foregoing, the laser beam scanning mechanism according to the present invention makes it possible to perform high-speed and highly efficient laser beam scanning even in the deep-ultraviolet region.

Figure 29:
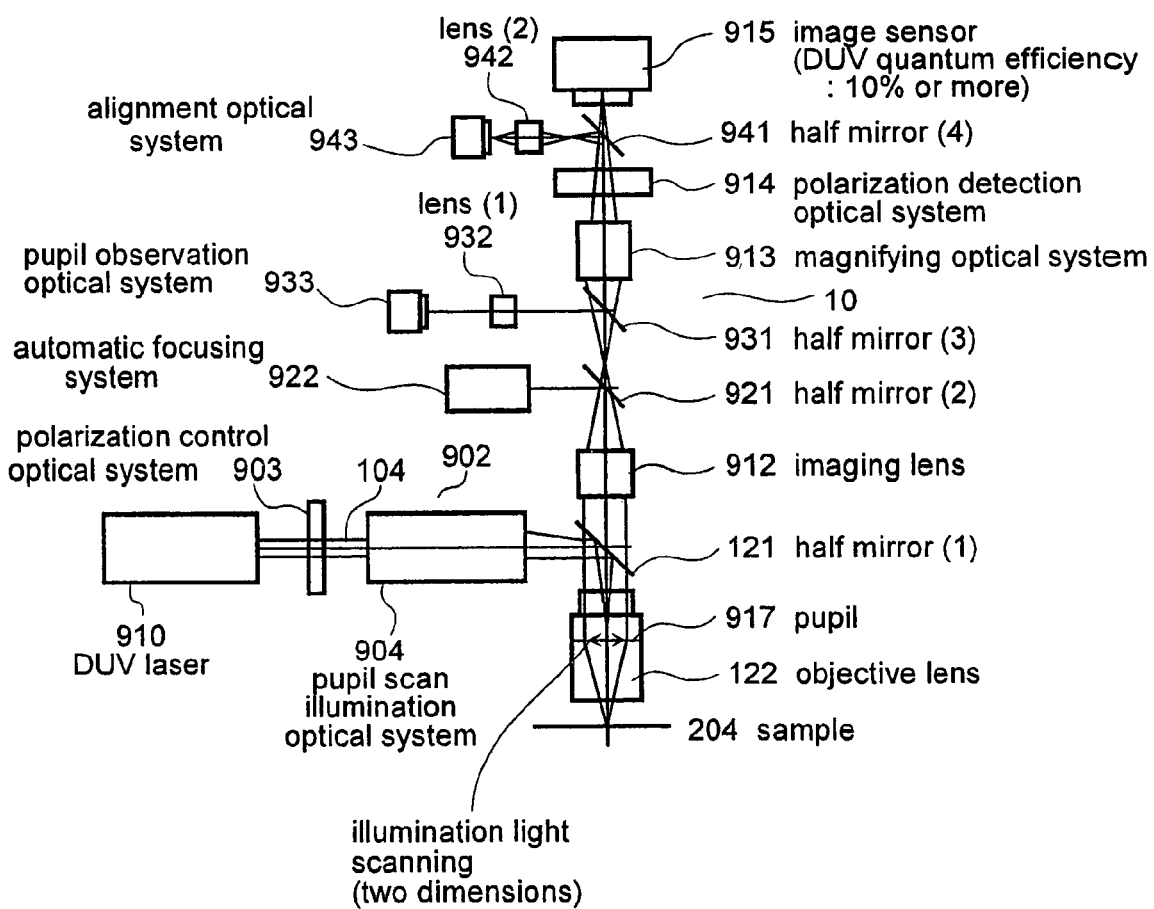
FIG. 29 is a diagram showing a second embodiment of the pattern defect detecting equipment equipped with the laser beam scanning mechanism according to the present invention.

Next, referring to FIG. 29, an embodiment of defect detecting equipment equipped with a laser beam scanning mechanism selected from the first embodiment to the fifth embodiment described above will be described. This embodiment is constructed with an epi-illumination system. It is understood that the illumination system may be constructed with oblique illumination. Further, as an illumination light source 1, for example, a DUV (deep ultraviolet rays) laser (for example, KrF excimer laser=248 nm, ArF excimer laser=198 nm, etc.) is used. As described, a DUV (deep ultraviolet ray) laser beam has a shorter wavelength and hence a high resolution, so that an optical image based on scattered light or diffracted light from a defect such as submicroscopic foreign particles having a dimension of 0.1 μm or less etc. can be obtained.

Therefore, an illumination system 902 is constructed with: an illumination light source 910, such as a DUV laser; a polarization control optical system for setting a polarization condition of the laser beam 104; a pupil scan illumination optical system 904 consisting of either one of the above-described first to fifth embodiments for scanning a laser beam over the pupil 917 of the objective lens 122; and a half mirror (1)121. A basic construction of a detecting optical system 900 comprises: the objective lens 122; an imaging lens 912; a magnifying optical system 913; a polarization detecting optical system 914 for setting a polarization condition of detected light in front of an image sensor 915(801) and the image sensor 915(801) having DUV quantum efficiency of around 10% or more. By the way, the polarization detecting optical system 914 in the detecting optical system 900 is used to shield specula reflected light (zero-th order diffraction light) from the object (sample object) 204 and can be constructed with a spatial filter instead. In this case, instead of the polarization detecting optical system 903 in the illumination optical system 902, it is necessary to provide, for example, a ring-zone illumination optical system with the use of light sources arranged in an orbicular zone around a central axis of the optical system (secondary light source).

Further, a half mirror (2)921 is disposed on a detection optical path, and an automatic focusing system 922 is provided for adjusting a surface of the sample object 204 on a focus of the objective lens 122. Further, a half mirror (3)931 is disposed so as to construct an optical system capable of observing a position of the pupil of the objective lens 122 with a lens (1)932 and a pupil observation optical system 933. Further, a half mirror (4)941 is disposed so as to construct an optical system capable of observing and aligning a pattern on the sample object 204 with a lens (2)942 and an alignment optical system 943.

Consequently, a DUV laser beam emitted from the illumination light source 910 is converted into linearly polarized light by, for example, the polarization control optical system 903 and is scanned two-dimensionally over the pupil 917 of the objective lens 122 for performing irradiation by the pupil scan illumination optical system 904. The reflected light from the sample object 204 is transmitted through the half mirror (1)905 after passing through the pupil 917 of the objective lens 122 and forms an enlarged optical image of the sample 204 on the image sensor 915(801) through the imaging lens 912 and the magnifying optical system 913. By the way, the image sensor 915(801) can be configured to detect an image formed only with scattered light or a component of diffracted light from the surface of the sample object 204 by shielding a linearly polarized component of the specula reflected light (zero-th order diffraction component) from the sample object 204, for example, by means of the polarization detecting optical system 914.

Figure 30:
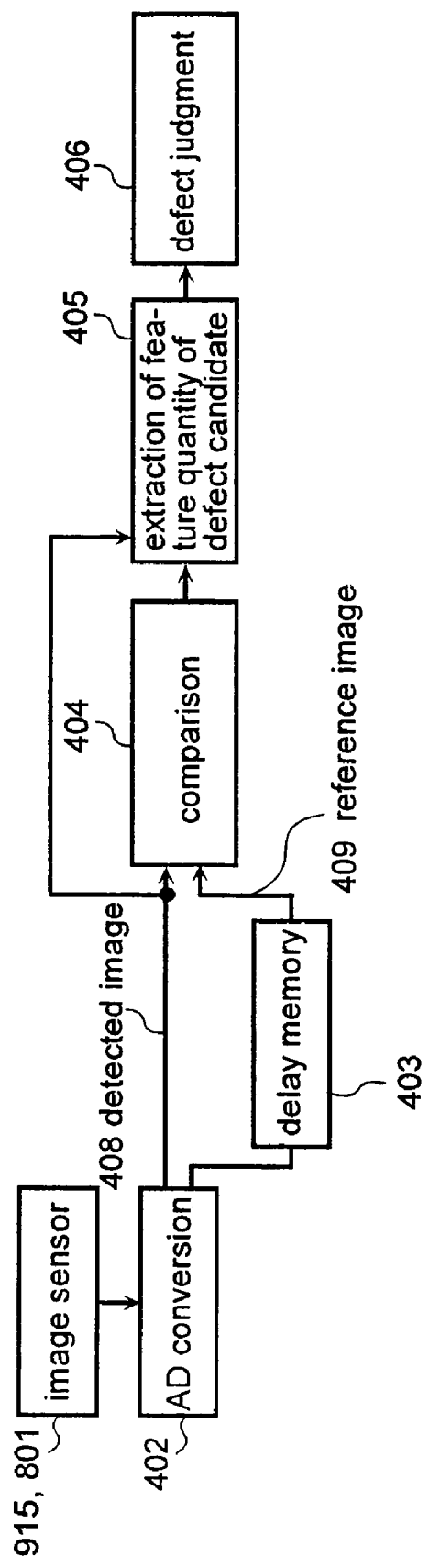
FIG. 30 is a block diagram showing a signal processing system in the pattern defect detecting equipment shown in FIG. 29.

Next, referring to FIG. 30, a signal processing system is described. That is, the signal processing system is composed of: an AD converter circuit 402 for analog-to-digital conversion of an image signal represented by grayscale values formed by accumulation of signals from each column of pixels obtained from the image sensor 915(801), which is composed of sensor elements having DUV quantum efficiency of around 10% or more, for example, a TDI image sensor, in synchronization with translation of the test object 204 in the Y-direction; a delay memory 403 for delaying a digital image signal outputted from the AD converter circuit by an amount corresponding to, for example, 1 chip (or plural pitches) of a circuit pattern repeated in the Y-direction; a comparator circuit 404 for extracting a signal, for example, a difference image signal, by comparing a digital detected image signal 408 obtained from the above-mentioned AD converter circuit 402 and a digital reference image signal 409 which was delayed by, for example, the amount of 1 pitch through the delay memory 403, and binarizing this extracted difference image signal using a predetermined threshold value to form a binarized image signal indicating defect candidates, such as foreign particles, a circuit pattern defect, etc.; a feature quantity extracting circuit 405 for extracting a feature quantity of a defect candidate, such as an area, location coordinates, a maximum length (for example, projected lengths to the X-axis direction and the Y-axis direction), moment, etc. based on the binarized image signal obtained from the comparator circuit 404 indicating defect candidates, such as foreign particles etc.; and a defect judging circuit 406 for judging a defect candidate as a defect when the feature quantity of the defect candidate extracted by the feature quantity extracting circuit 405 surpasses a predetermined criterion. By the way, regarding the feature quantity, at a time when a certain feature is identified as a defect candidate, a grayscale value based on a digital detected image signal obtained from the AD converter circuit 402 may be added to an original feature quantity to extract a three-dimensional feature quantity.

Especially, in order to detect a defect such as submicroscopic foreign particles of a size of around 0.1 μm or less etc., it is necessary to remove noise components, due to minute irregularities of the surface and the underlying pattern of the test object 204, out of the signal to prevent erroneous detection. To this end, a real submicroscopic defect, such as foreign particles etc. can be detected through the steps of: extracting any difference image signal surpassing a predetermined threshold as a defect candidate; and discriminating whether an extracted signal is a true defect, such as foreign particles etc., or false information arising from a minute irregularity of the surface or an underlying pattern according to the extracted feature quantity of each defect candidate.

According to the present invention, since a UV laser or DUV laser beam having a short wavelength can be used after its coherence is reduced, a defect of a circuit pattern having a pattern width as small as 0.2 μm or less can be detected with sufficient accuracy.

By virtue of the present invention, since high-illuminance UV light emitted from a laser source can be used to irradiate a sample after its coherence has been reduced, a higher-resolution image can be obtained compared to a case where conventional visible light is used as illumination light, and hence a defect can be detected with high sensitivity.

What is claimed is:

1. An inspection apparatus, comprising:
   an emitter device which emits an ultraviolet laser beam;
   an illumination optical system having a polarization controller and an objective lens, for illuminating a specimen with a polarization condition controlled ultraviolet laser beam through the objective lens;
   a detection optical system having a sensor for detecting light from the specimen illuminated by said polarization condition controlled ultraviolet laser beam through the illumination optical system; and
   a processor which processes a signal outputted from said sensor and detects a defect on said specimen;
   wherein the illumination optical system includes a coherence reducer which reduces coherency of the ultraviolet laser beam emitted from said emitter.

2. A method for inspecting a specimen, comprising the steps of:
   emitting an ultraviolet laser beam form an emitter;
   controlling a polarization condition of the emitted ultraviolet laser beam;
   illuminating a specimen with the polarization condition controlled ultraviolet laser beam through an objective lens;
   reducing coherence of the polarization condition controlled ultraviolet laser beam before illuminating the specimen
   detecting light from the specimen illuminated by the polarization condition controlled ultraviolet laser beam with a sensor; and
   processing a signal outputted from the sensor and detecting a defect on said specimen.

3. An inspecting apparatus according to the claim 1, wherein the ultraviolet laser beam has a wavelength range less than 300 nm.

4. An inspection apparatus according to the claim 1, wherein the detection optical system detects an image of the specimen by the detection of light from the specimen.

5. The method for inspecting a specimen according to the claim 2, wherein the ultraviolet laser beam has a wavelength range less than 300 nm.

6. A method for inspecting a specimen according to the claim 2, wherein in the step of detecting, an image of light reflected from the specimen is detected with the sensor.

* * * * *